(12) United States Patent
Zhao

(10) Patent No.: US 7,759,125 B2
(45) Date of Patent: *Jul. 20, 2010

(54) PHOTOELECTROCHEMICAL DETERMINATION OF CHEMICAL OXYGEN DEMAND

(75) Inventor: Huijun Zhao, Highland Park (AU)

(73) Assignee: Aqua Diagnostic Pty Ltd, South Melbourne (AT)

( * ) Notice: Subject to any disclaimer, the term of this patent is extended or adjusted under 35 U.S.C. 154(b) by 0 days.

This patent is subject to a terminal disclaimer.

(21) Appl. No.: 12/538,994

(22) Filed: Aug. 11, 2009

(65) Prior Publication Data

US 2010/0032282 A1    Feb. 11, 2010

Related U.S. Application Data

(60) Division of application No. 11/270,445, filed on Nov. 10, 2005, now Pat. No. 7,598,086, which is a continuation-in-part of application No. 10/551,689, filed as application No. PCT/AU2004/000438 on Apr. 5, 2004, now abandoned.

(30) Foreign Application Priority Data

Apr. 4, 2003   (AU) ............................... 2003901589

(51) Int. Cl.
    *G01N 33/18*      (2006.01)
(52) U.S. Cl. .................. 436/62; 436/133; 436/146; 436/150; 436/159; 436/905; 422/82.02; 422/82.12; 422/78
(58) Field of Classification Search ....................... None
See application file for complete search history.

(56) References Cited

U.S. PATENT DOCUMENTS

4,868,127 A    9/1989   Blades et al.

(Continued)

FOREIGN PATENT DOCUMENTS

CN      1412540 A     4/2003

(Continued)

OTHER PUBLICATIONS

Jiang et al., J. Phys. Chem. B 2003, 107, 12774-12780.
Jiang et al., Journal of Photochemistry and Phobiology A: Chemistry 156 (2003) 201-206.

*Primary Examiner*—Yelena G Gakh
*Assistant Examiner*—Robert Xu
(74) *Attorney, Agent, or Firm*—Connolly Bove Lodge & Hutz LLP

(57) ABSTRACT

A photoelectrochemical assay apparatus and method for determining chemical oxygen demand (COD) of a water sample is described. The photoelectrochemical assay comprises:
   a) a measuring cell for holding a sample to be analysed
   b) a titanium dioxide nanoparticle photoelectric working electrode and a counter electrode disposed in said cell,
   c) a UV light source adapted to illuminate the photoelectric working electrode
   d) control means to control the illumination of the working electrode
   e) potential measuring means to measure the electrical potential at the working and counter electrodes
   f) analysis means to derive a measure of oxygen demand from the measurements made by the potential measuring means.

17 Claims, 19 Drawing Sheets

U.S. PATENT DOCUMENTS

| | | |
|---|---|---|
| 6,102,545 A | 8/2000 | Ogino |
| 2004/0108197 A1 | 6/2004 | Buhr |
| 2006/0173352 A1 | 8/2006 | Lilge et al. |

FOREIGN PATENT DOCUMENTS

| | | |
|---|---|---|
| EP | 282441 A2 | 9/1988 |
| EP | 834739 A2 | 4/1998 |
| JP | 06148172 A | 5/1994 |

(a)

(b)

(c)

PHOTOELECTROCHEMICAL DETERMINATION OF CHEMICAL OXYGEN DEMAND

CROSS-REFERENCE TO RELATED APPLICATIONS

This application is a Divisional of application Ser. No. 11/720,445 filed on Nov. 10, 2005 (allowed), which is a continuation-in-part of application Ser. No. 10/551,689 filed Sep. 30, 2005 (abandoned), which is a national phase of PCT/AU04/00438 filed Apr. 5, 2004 and for which priority is claimed under 35 U.S.C. §120; and this application claims priority of Application No. 2003901589 filed in Australia on Apr. 4, 2003 under 35 U.S.C. §119. The entire contents of these applications are hereby incorporated by reference.

FIELD OF THE INVENTION

This invention relates to a new method for determining oxygen demand of water using photoelectrochemical cells. In particular, the invention relates to a new photoelectrochemical method of determining chemical oxygen demand of water samples using a titanium dioxide nanoparticulate semiconductive electrode.

BACKGROUND OF THE INVENTION

Nearly all domestic and industrial wastewater effluents contain organic compounds, which can cause detrimental oxygen depletion (or demand) in waterways into which the effluents are released. This demand is due largely to the oxidative biodegradation of organic compounds by naturally occurring microorganisms, which utilize the organic material as a food source. In this process, carbon is oxidised to carbon dioxide, while oxygen is consumed and reduced to water.

Standard analytical methodologies for the determination of aggregate properties such as oxygen demand in water are biochemical oxygen demand (BOD) and chemical oxygen demand (COD). BOD involves the use of heterotrophic microorganisms to oxidise organic material and thus estimate oxygen demand. COD uses strong oxidising agents, such as dichromate or permanganate, to oxidise organic material. BOD analysis is carried out over five days and oxygen demand determined by titration or with an oxygen probe. COD measures dichromate or permanganate depletion by titration or spectrophotometry.

Despite their widespread use for estimating oxygen demand, both BOD and COD methodologies have serious technological limitations. Both methods are time consuming and very expensive, costing water industries and local authorities in excess of $1 billion annually worldwide. Other problems with the BOD assay include: limited linear working range; complicated, time consuming procedures; and questionable accuracy and reproducibility (the standard method accepts a relative standard deviation of ±15% for replicate $BOD_5$ analyses). More importantly, interpretation of BOD results is difficult since the results tend to be specific to the body of water in question, depend on the pollutants in the sample solution and the nature of the microbial seed used. In addition, the BOD methodologies cannot be used to assess the oxygen demand for many heavily polluted water bodies because of inhibitory and toxic effects of pollutants on the heterotropic bacteria.

The COD method is more rapid and less variable than the BOD method and thus preferred for assessing the oxygen demand of organic pollutants in heavily polluted water bodies. Despite this, the method has several drawbacks in that it is time consuming, requiring 2-4 hours to reflux samples, and utilises expensive (e.g. $Ag_2SO_4$), corrosive (e.g. concentrated $H_2SO_4$) and highly toxic (Hg(II) and Cr(VI)) reagents. The use of toxic reagents being of particular environmental concern, leading to the Cr(VI) method being abandoned in Japan.

Titanium(IV) oxide ($TiO_2$) has been extensively used in photooxidation of organic compounds. $TiO_2$ is non-photocorrosive, non-toxic, inexpensive, relatively easily synthesised in its highly catalytic nanoparticulate form, and is highly efficient in photooxidative degradation of organic compounds.

Fox M. A. and Tien, T, Anal. Chem., (60 1988) 2278-2282 investigated the development of a photoelectrochemical detector by employing an anodically formed $TiO_2$ electrode for use in high-pressure liquid chromatography. This photoelectrochemical detector is reported as being sensitive to oxidisable organics, such as alcohols. The electrode system developed by Fox et al had low photocatalytic efficiency of the system and is difficult to use as it cannot discriminate between the respective currents generated from the oxidation of water and organic matter.

Brown, G. N., et al., Anal. Chem., 64 (1992) 427-434 investigated the use of a photoelectrochemical detector by employing a thermally formed $TiO_2$ electrode for use as a detector in flow injection analysis and liquid chromatography. The detector was found to be non-selective in its response to a variety of organic analytes. Brown et al found that the response of the detector varied with temperature, duration of heating, oxidative atmosphere, etching of the titanium wire electrode, amount of doping on the $TiO_2$ detector and solvents. Similar to Fox et al this electrode system had low photocatalytic efficiency and cannot discriminate between the currents generated from the oxidation of water and organic matter.

Matthews R. W. et al., Analytica Chimica Acta 233 (1990) 171-179 (also the subject of Australian patent 597165) utilised a $TiO_2$ photocatalytic oxidation system to determine total carbon in water samples, by placing $TiO_2$ into a slurry or suspension, photooxidising the organic material with in the sample to evolve carbon dioxide ($CO_2$). The evolved $CO_2$ was measured to predict TOC value of the sample. Matthews found that the total organic carbon can be estimated from the total amount of carbon dioxide purged from photocatalytic cell.

Jiang D. et al., J. Photochem & Photobio A: Chemistry 144 (2001) 197-204 also investigated the photoelectrochemical behaviour of nanoporous $TiO_2$ film electrodes in the photooxidation of methanol. This paper discloses a model experimental system to study the kinetics of photocatalytic water remediation on $TiO_2$ particles. Jiang found that the photocurrent response of the electrode was greatly influenced by applied potential, light intensity, methanol concentration and pH. A linear relationship was found to exist between the photocurrent produced through the photo-oxidation of methanol and the concentration of methanol in the sample. However, as concentration of methanol increased the migration of photoelectrons across the $TiO_2$ film and therefore photogenerated charge separation becomes a rate-limiting step, thus limiting the working range in which the linear relationship between photocurrent and concentration occurs.

Lee Kyong-Hoon et al., Electroanalysis 12, No 16 (2000) 1334-1338, investigated the determination of COD using a microfabricated Clark-type oxygen electrode and $TiO_2$ fine particles suspended in a sample solution under photocatalytic oxidative degradation conditions. The current generated from the oxygen electrode under −800 mV applied potential was used to indicate the oxygen concentration change before and after the photooxidation. The change in oxygen concentration was then correlated to COD value of the sample.

Kim, Yoon-Chang, et al., Anal. Chem., 72 (2000) 3379-3382; Analytica Chimica Acta 432 (2001) 59-66 and Anal. Chem., 74 (2002) 3858-3864 all relate to the determination of COD using a photocatalytic oxidative degradation of organic compounds at a titanium dioxide particles. In Anal. Chem., 2000, Kim et al investigated the use of translucent poly(tetrafluoroethylene) (PTFE) membrane having fine particles of $TiO_2$ absorbed or entrapped onto the surface of the membrane in combining with a oxygen electrode as a possible COD sensor. The immobilised $TiO_2$ particles serve as an oxidation reagent and the analytical signal was based on the oxygen concentration measurements between the working and reference oxygen electrodes.

Calibration curves where established using sodium sulfite ($Na_2SO_3$), prior to determining COD of analytes. In this study Kim et al reports that the membrane sensor did not show good reproducibility.

In Analytica Chimica Acta 432 (2001) 59-66, Kim et al investigated the use of titanium dioxide ($TiO_2$) beads in a photochemical column and an oxygen electrode as the sensor in determining dissolved oxygen from the photocatalytic oxidation of organic compound and thus the COD value of the analyte.

In Anal. Chem., 74 (2002) 3858-3864 Kim et al investigated the use of 0.6 mm $TiO_2$ beads in a quartz tube in the determination of oxygen consumption from photochemical oxidation of organic compounds and subsequent calculation of COD values from the difference in the currents recorded at the reference and working oxygen electrodes.

The methods described by Lee et al and Kim et al above all utilise $TiO_2$ as an oxidative reagent to replace the traditional reagent used in COD such as chromate salts, with the analytical signal being obtained via two traditional oxygen electrodes. There are many disadvantages of their method, which makes the practical application of the method very difficult.

To date the COD assay methodologies of the prior art are indirect in their analysis methods requiring calibration and often suffer from having low sensitivity, poor accuracy, narrow linear working ranges and/or difficult to operate. More importantly, these prior art COD assay methodologies are matrix dependent due to the low oxidation efficiency. It is an object of this invention to overcome these shortcomings.

SUMMARY OF THE INVENTION

To this end this invention provides a method of determining chemical oxygen demand of a water sample, comprising the steps of a) applying a constant potential bias to a photoelectrochemical cell, having a photoactive working electrode and a counter electrode, and containing a supporting electrolyte solution;

b) illuminating the working electrode with a light source, preferably a UV light source, and recording the background photocurrent produced at the working electrode from the supporting electrolyte solution;

c) adding a water sample, to be analysed, to the photoelectrochemical cell;

d) illuminating the working electrode with a UV light source and recording the total photocurrent produced;

e) determining the chemical oxygen demand of the water sample according to the type of degradation conditions employed.

The working electrode may be formed from any nanoparticulate semiconductive material capable of photooxidation of organic compounds. The nanoparticulate semiconductive electrode may be selected from titanium dioxide, niobium pentoxide, strontium titanate, indium trioxide, calcium titanate, tungsten trioxide, barium titanate, ferric oxide, zinc oxide, potassium tantalate, tin dioxide, cadmium oxide, hafnium oxide, zirconium oxide, tantalum pentoxide, chromium trioxide or yttrium trioxide. Preferably the semiconductive electrode is titanium dioxide. More preferably the semiconductive electrode is formed by laying nanoparticles of titanium dioxide on an inert substrate, such as conducting glass.

This invention is partly predicated on the insight that the methods described in the prior art, utilising photoelectrochemical properties of $TiO_2$ nanoparticle semiconductive electrodes provide for the direct determination of COD. In the prior art method, the method relies for accuracy on the two oxygen electrodes, which have to be identical in responding to the oxygen change. In addition, the prior art method cannot be used for low COD samples due to the insufficient sensitivity of the method. Low COD content is important in testing water for suitability in drinking and cleaning applications. By using this technique the measurement of milliamperes of current allows much greater sensitivity in the low COD range.

The method of determining the chemical oxygen demand value of a water sample may be determined under exhaustive degradation conditions, in which all organics present in the water sample are oxidised. Under exhaustive degradation conditions the chemical oxygen demand value can be obtained according to the steps of;

a) integrating both the background photocurrent and total photocurrent ($i_t(1)$) to give the background charge and total charge, and subtracting the background charge from the total charge to determine the net charge $Q_{net}$; for the water sample; and b) calculating the chemical oxygen demand value utilising formula (I);

$$COD(mg/L \text{ of } O_2) = \frac{Q_{net}}{4FV} \times 32000 \qquad (1)$$

wherein $Q_{net}$=net charge

F=Faradays constant

V=sample volume

The method of determining the chemical oxygen demand value of a water sample may be determined under non-exhaustive degradation conditions, in which the organics present in the water sample are partially oxidised. Under non-exhaustive degradation conditions, all photocurrent are measured under the diffusion controlled conditions and the method of determining oxygen demand value may further include the steps of;

adding a standard solution, having known organic concentration or chemical oxygen demand value, to the photoelectrochemical cell containing the water sample to be analysed;

illuminating working electrode with a UV light source and recording the limiting photocurrent produced from the partial oxidative degradation of the standard solution ($i_l(2)$); and determining the chemical oxygen demand value by;

a) calculating the current for the water sample by subtracting the limiting background photocurrent ($i_{lbackground}$) from the limiting photocurrent of the sample ($i_l(1)$) at a predetermined illumination time according to the formula $$i_{lsample} = i_l(1) - i_{lbackground},$$

b) calculating the limiting photocurrent for the standard solution by subtracting the background photocurrent ($i_{lbackground}$) from the limiting photocurrent of the sample and standard ($i_l(2)$) at the predetermined illumination time according to the formula:

$$i_{lstandard} = i_l(2) - i_{lbackground}$$

c) determining the chemical oxygen demand value of the sample solution according the following sequence of computations:

$$i_{lstandard} = nFAk[COD]_{sample} = K[COD]_{sample}$$

$$i_{lstandard} = nFAk\{[COD]_{sample} + [COD]_{standard}\} = K\{[COD]_{sample}[COD]_{standard}\} \text{ where } K = nFAk \text{ is a constant for given experimental conditions}$$

n=number of electrons transferred during the photoelectrochemical degradation,
F=Faraday constant,
A=active electrode area,
k=mass-transfer coefficient; and $$[COD]_{sample} = \frac{i_{lsample}}{i_{lstandard} - i_{lsample}} \times [COD]_{standard}$$

The method steps for both the exhaustive and non-exhaustive degradation condition may be repeated as many times as required to analyse all necessary water samples.

The potential bias applied to the electrodes is preferably between −0.1V and +0.5V. More preferably the potential difference is between approximately +0.15V and +0.35V.

A supporting electrolyte is used to determine the background photocurrent and to dilute the water sample to be tested. The determination of the background photocurrent measures the oxidation of water and this can be deducted from the sample reading to give the photocurrent due to the oxidation of organic material in the sample. This measurement may be made as a separate measurement to the sample reading or when conducting an exhaustive degradation the final steady current after the oxidation is completed is a measure of the background photo current. The supporting electrolyte may be selected from sodium nitrate, sodium perchlorate or any other electrolytes that are electrochemically and photoelectrochemically stable under the experimental conditions and do not absorb UV radiation in the range being used. The dilution of the samples enables the method to have a wide linear range while still keeping the test duration to a relatively small period.

The water sample is preferably illuminated by a light source having a photo intensity of between 1 and 100 mWcm$^{-2}$. More preferably the frequency of the light source is between approximately 6-9.5 mWcm$^{-2}$.

In another aspect the present invention provides a photoelectrochemical assay apparatus for determining oxygen demand of a water sample which consists of
a) a measuring cell for holding a sample to be analysed
b) a photoactive working electrode and a counter electrode disposed in said cell,
c) a light source, preferably a UV light source, adapted to illuminate the photoactive working electrode
d) control means to control the illumination of the working electrode, the applied potential and signal measurement
e) current measuring means to measure the photocurrent at the working and counter electrodes
f) analysis means to derive a measure of oxygen demand from the measurements made by the photocurrent measuring means.

Preferably a reference electrode is also located in the measuring cell and the working electrode is a nanoparticulate semiconductive electrode preferably titanium dioxide.

In other embodiments the measuring cell may be a stationary cell with different cell geometry and volume, or a flow through cell with different cell geometry and volume, and with a flow rate adjusted to optimise the sensitivity of the measurements.

It is preferred to use a thin film small diameter circular reaction chamber with a small reaction chamber volume as gas bubble entrapment is avoided, and photo utilisation efficiency is high.

In another aspect this invention provides electrophotochemical reaction cell for use in the apparatus of this invention which consists of
a) cell body containing a sample inlet and a sample outlet
b) a socket for a ultraviolet light emitting diode unit
c) a reference electrode
d) an optionally removable working electrode of titanium dioxide nanoparticles on an inert substrate.
e) a reaction chamber located between the working electrode and the socket for a ultraviolet light emitting diode unit.

The UV LED unit may include additional optical components such as lenses and optical fibres. It is preferred that the light source be a UV LED preferably a high power chip type UV LED, such as NCCU 033 produced by HICHIA. Such a UV source offers many advantages over traditional UV light sources. It has very compacted structure and small physical dimensions, requires little electrical power to operate and produces high light intensity. In addition, it possesses the longest operational life, highest stability and reproducibility among all UV light sources.

A High power chip type UV LED utilises a highly compacted configuration. As a result, a heat sink is required to counter the overheating problem. In some circumstances, especially when the array configuration is used, the physical size of the heat sink/LED combination makes the use of the LED difficult. Furthermore, in order to achieve maximum output power, the LED needs to be located very close to the object surface to be illuminated due to its inherent directivity characteristics. For example, the short distance (a few millimetre) between the LED and the object surface to be illuminated makes the implementing a shutter in between the two extremely difficult.

These problems can be overcome by employing one of the following embodiments.

A Micro-Directivity Regulator (MDR) consists of a set of small size optical lenses that configures in a way that allows the maximum collection of output light from the LED source and regulates the collected light into a uniformly distributed-parallel light. When a MDR is combined with the LED light source, a large distance between the LED and the surface to be illuminated is allowed since the output light intensity becomes distance independent.

The input light can be regulated into two different shapes of light beams. One is circular shape parallel beam and another is narrow-rectangular shape parallel beam The embodiment mentioned above provides the freedom of changing the distance, but not the direction. With this configuration, the light source must be located at the perfect position opposites to the object to be illuminated. Incorporation of an Optical Fibre Directivity Regulator (OFDR) provides freedoms for changing both distance and direction. It also allows the end of the light source to be immersed in the solution, which provides addition flexibility for the design of a photoreactor.

An OFDR consists of two sets of optical lenses. One set is located at the reception end and another set is located at the output end of the OFDR. Simply by adding a cylindrical lens to the output end can change the shape of the output beam from circular shape into narrow-narrow-rectangular shape.

Many applications require simultaneously operating multiple photoreactors and for these an Optical Fibre Directivity Regulative Array (OFDRA) may be used.

Under some circumstances, large input light power is needed to increase the rate of reaction or reduce the time required for the completion of the reaction. An OFDRA is capable of applying combined output powers of the OFDRA to a single reactor in a form of long-narrow continuous rectangular shape beam The measuring cell is intended to be robust enough for field use and for ease of maintenance a portion of the cell will be replaceable and similarly the supporting electrolyte can be provided in a an easily replaceable cartridge.

BRIEF DESCRIPTION OF DRAWINGS

To assist in understanding the invention preferred embodiments will now be described with reference to the following figures in which.

| 1 = p-chlorophenol; | 2 = potassium hydrogen phthalate; |
| 3 = methanol; | 4 = d-glucose; |
| 5 = malonic acid; | 6 = succinic acid; |
| 7 = glutaric acid; and | 8 = glycine. |

Photo intensity: 9.1 $mWcm^{-2}$; Applied potential bias: +0.20V vs Ag/AgCl.

Figure 10:
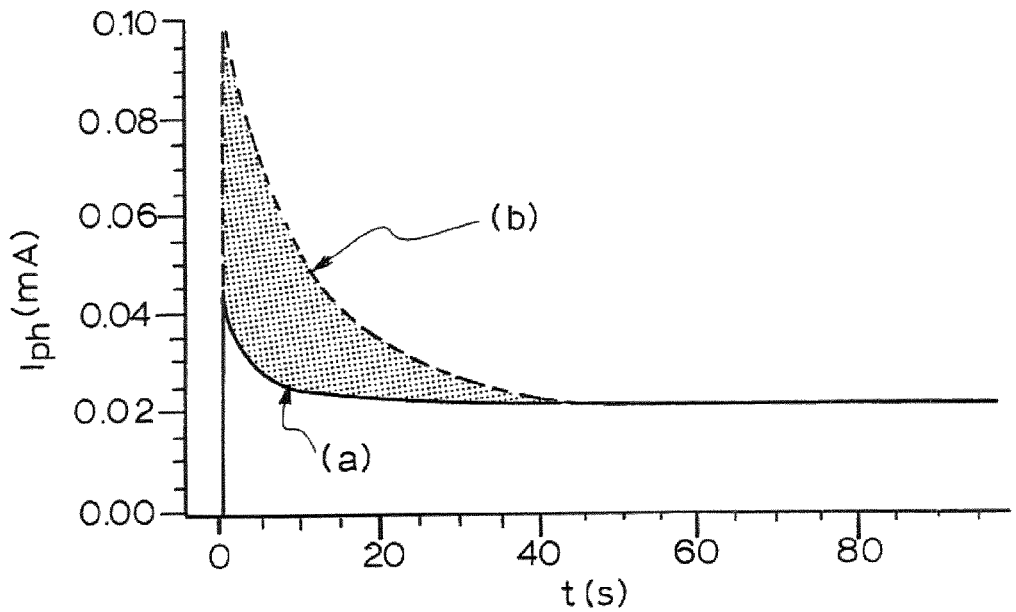

FIG. 10 Photocurrent response of (a) 0.10M $NaNO_3$ and (b) a solution containing potassium hydrogen phthalate and 0.1 M $NaNO_3$. Photo intensity: 9.1 $mWcm^{-2}$; Applied potential bias: +0.20V vs Ag/AgCl.

Figure 11:
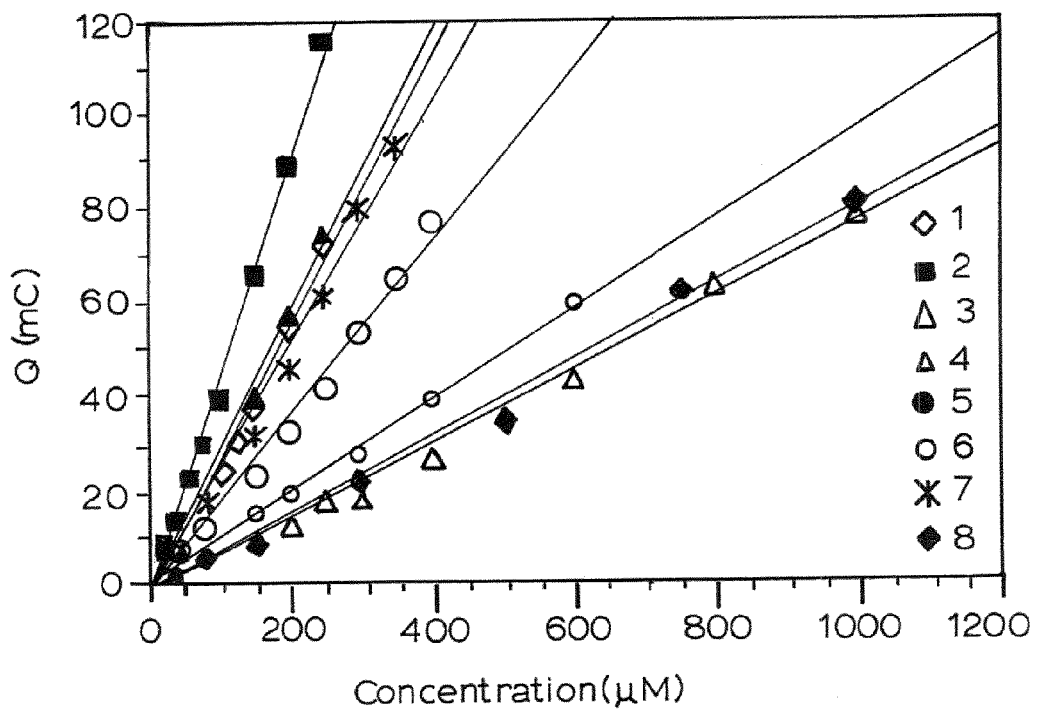

FIG. 11. Q-C curves for a range of organic compounds, namely;

| 1 = p-chlorophenol; | 2 = potassium hydrogen phthalate; |
| 3 = methanol; | 4 = d-glucose; |
| 5 = malonic acid; | 6 = succinic acid; |
| 7 = glutaric acid; and | 8 = glycine. |

Photo intensity: 9.1 $mWcm^{-2}$; Applied potential bias: +0.20V vs Ag/AgCl.

Figure 12:
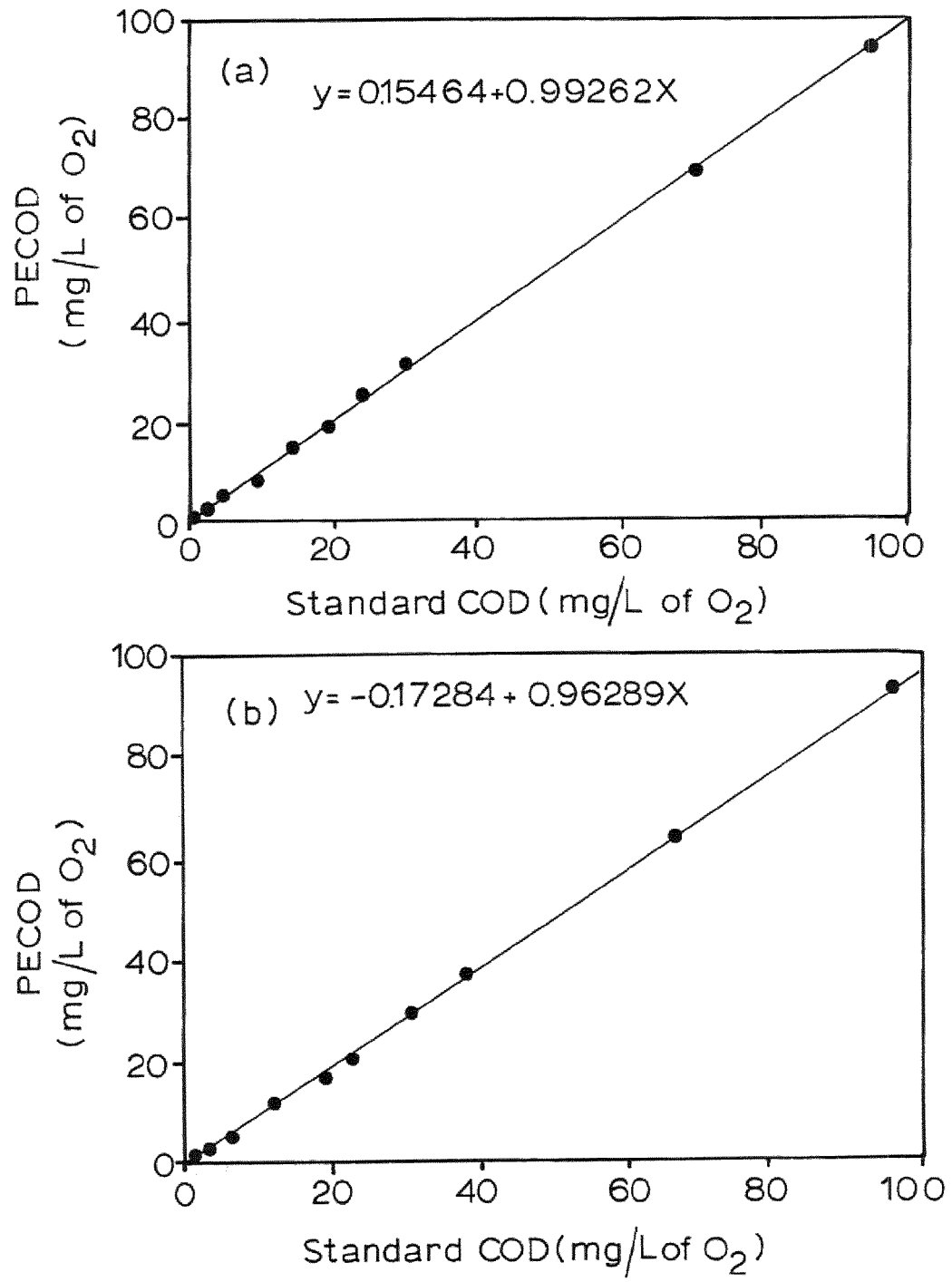

FIG. 12. Correlation between experimental COD value and standard COD value. (a) COD standard test solution (KHP); (b) a synthetic COD sample containing equal molar concentration of all compounds used in FIG. 8.

Figure 13:
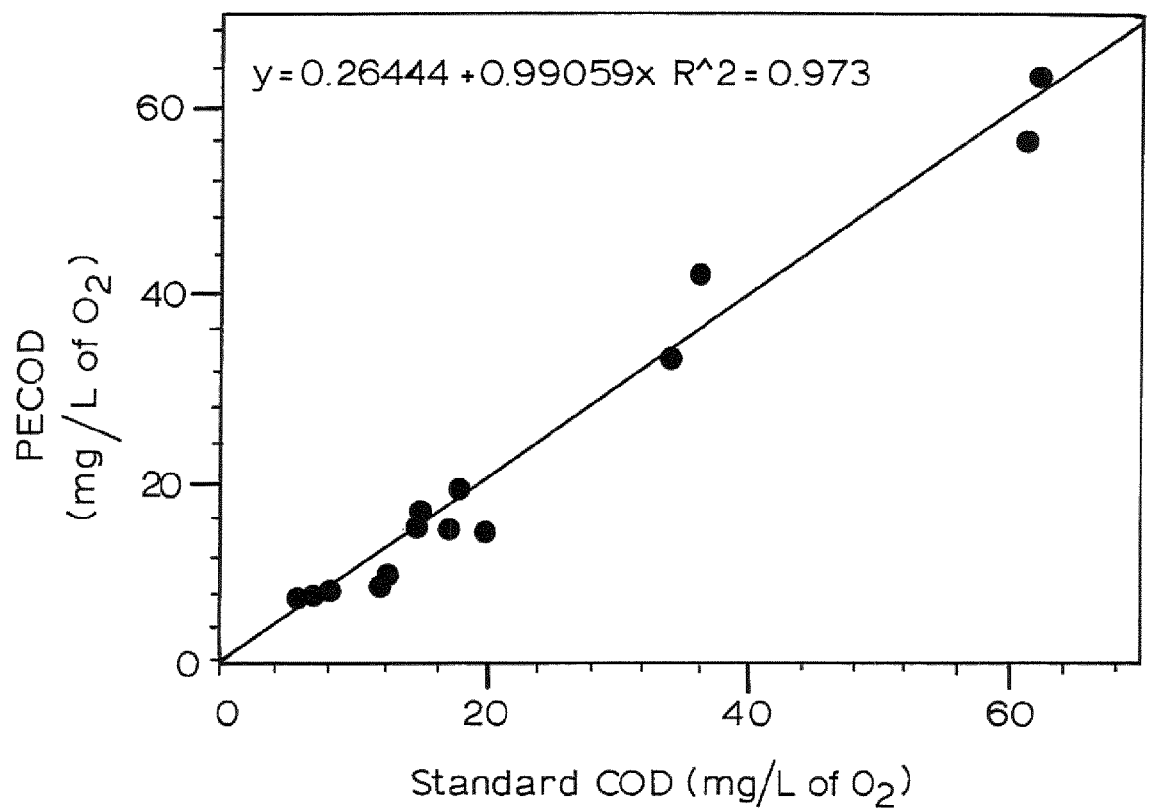

FIG. 13. Comparison of PECOD and conventional COD method (dichromate) in the detection of real samples.

Figure 14:
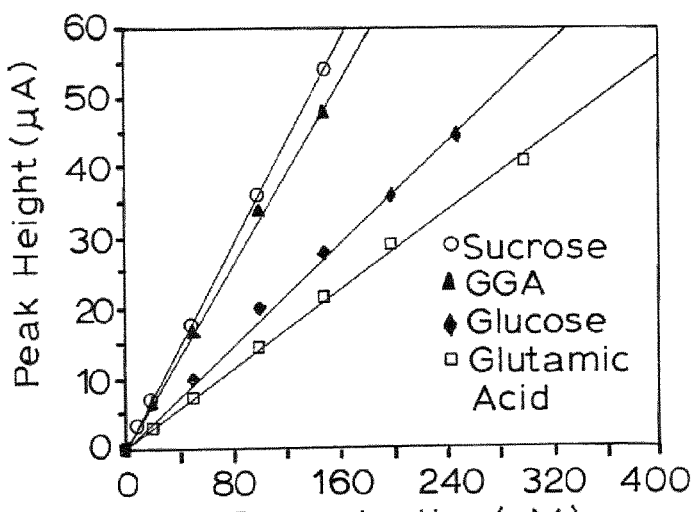
Figure 14:
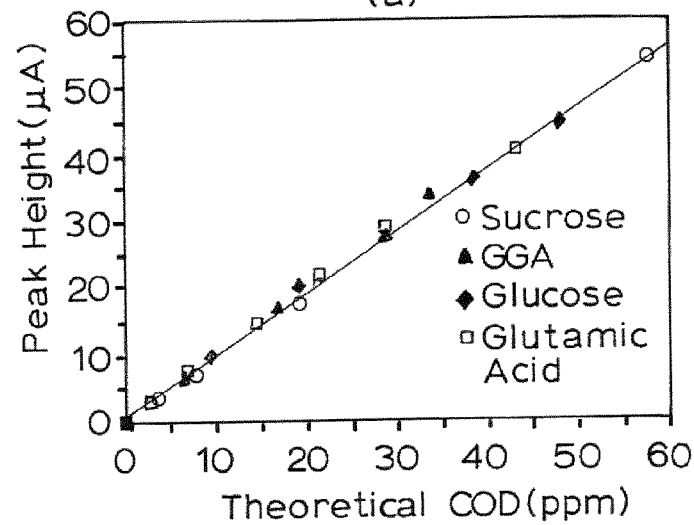
Figure 14:
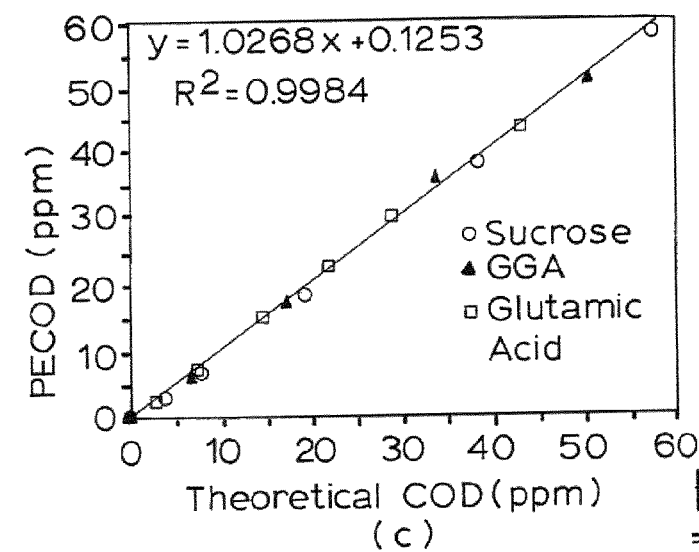
Figure 15:
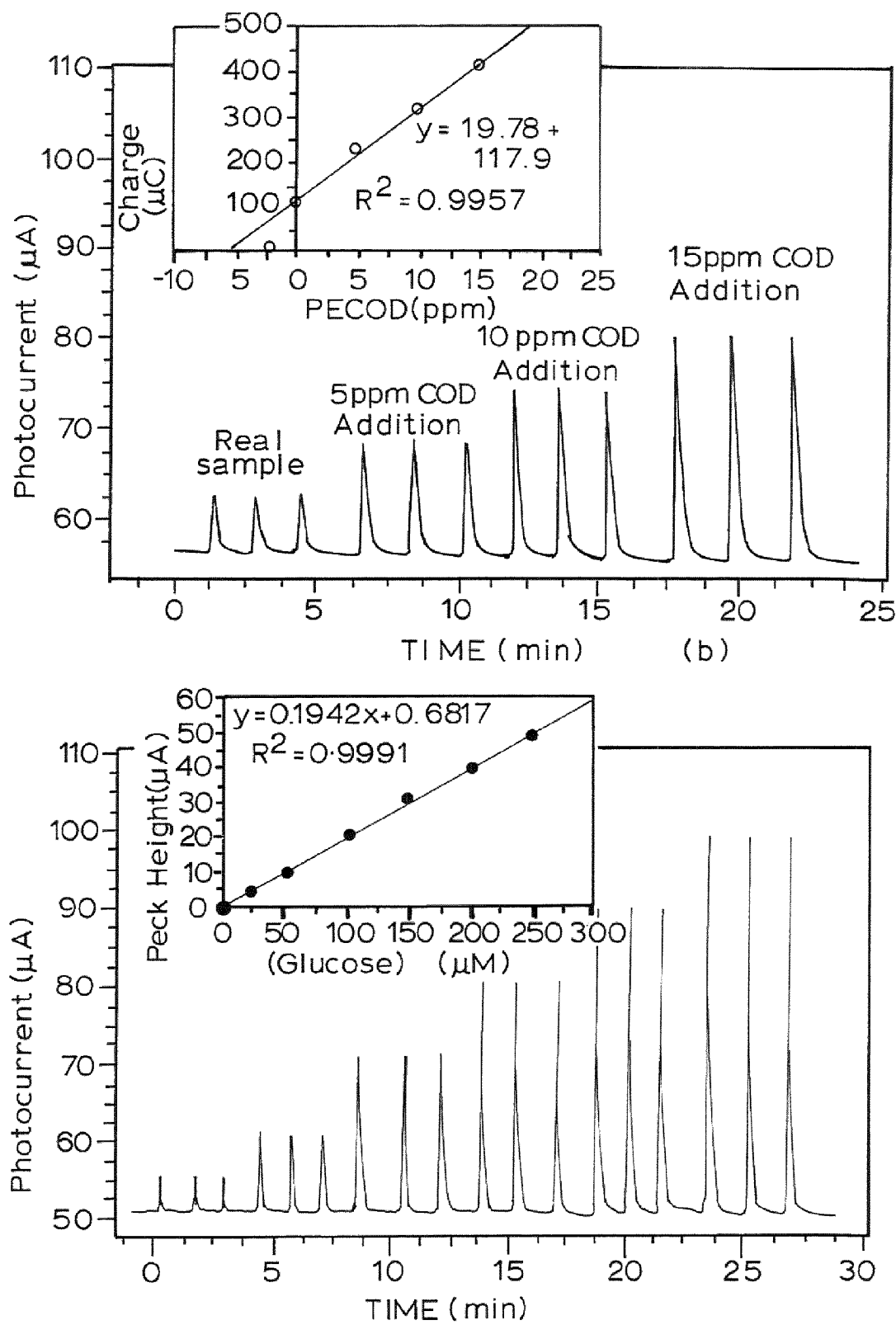

FIG. 14 Photoelectrochemical detection of synthetic examples showing peak height to concentration FIG. 15 Photoelectrochemical determination of COD value for the synthetic samples: (a) the quantitative relationship between the peak height and concentration (µM) of organic compounds. (b) the quantitative relationship between the peak height and theoretical COD. (c) the correlation between the PECOD and theoretical COD for the synthetic COD test samples.

Figure 16:
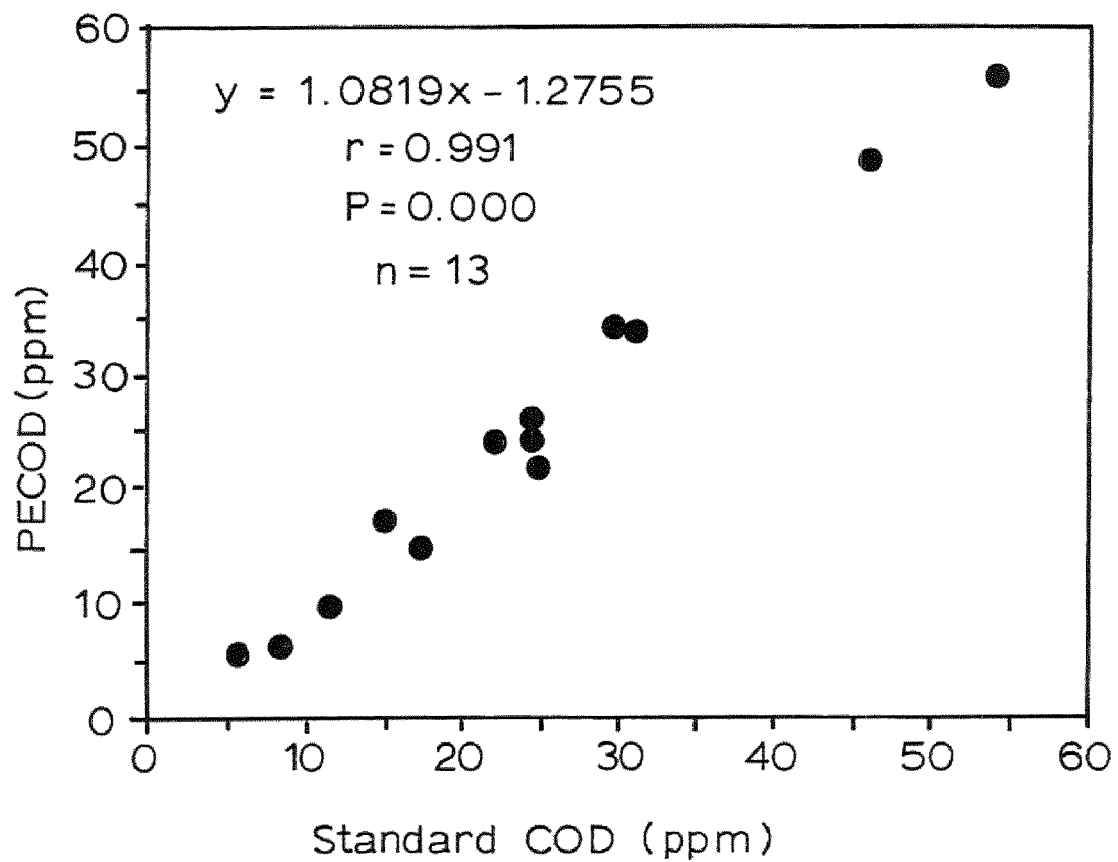
Figure 17:
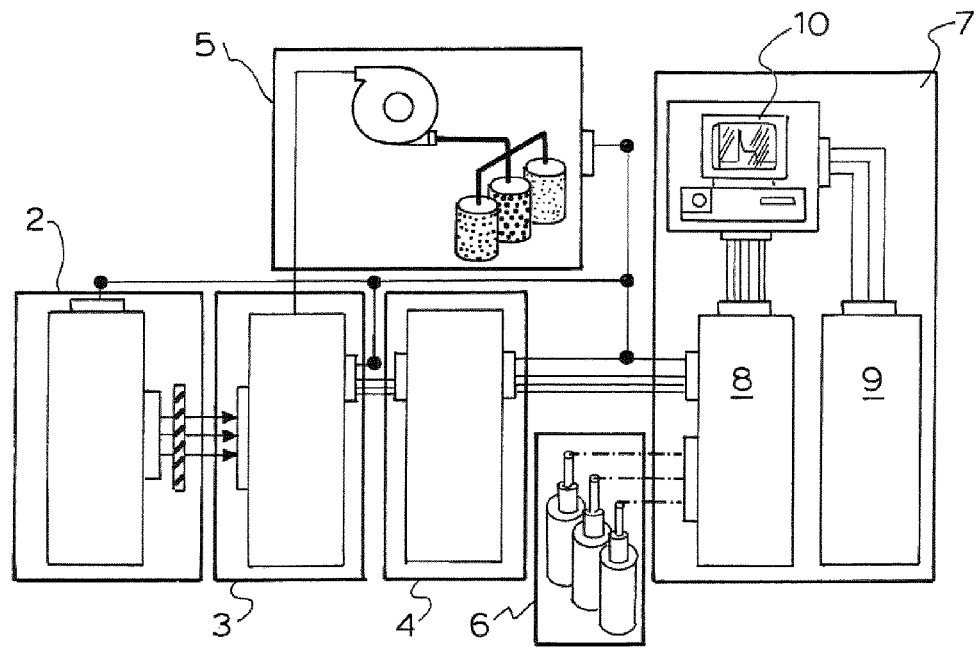
Figure 18:
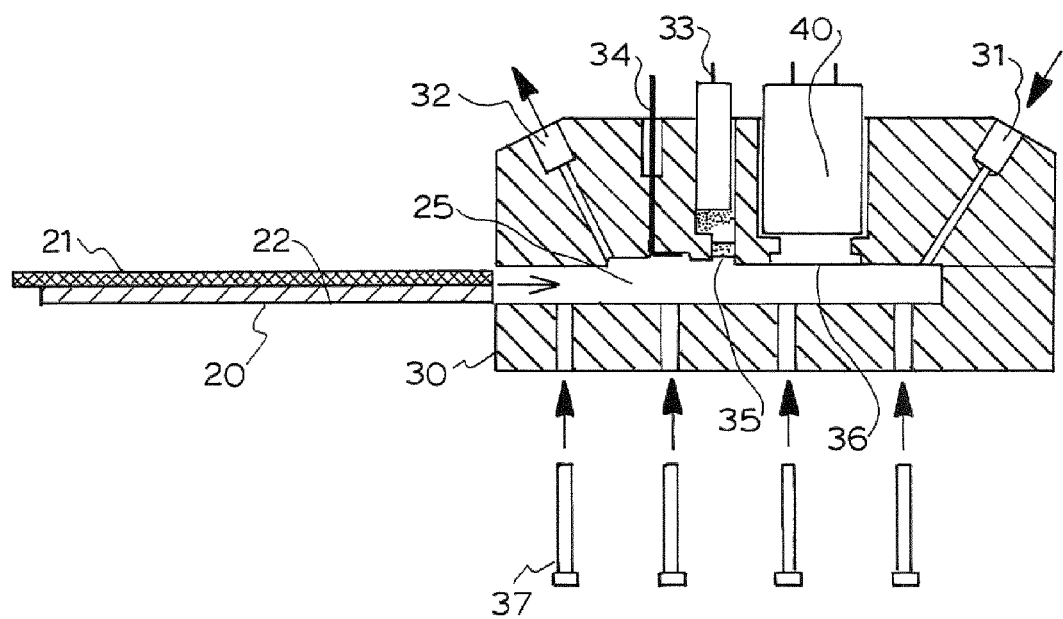
Figure 19:
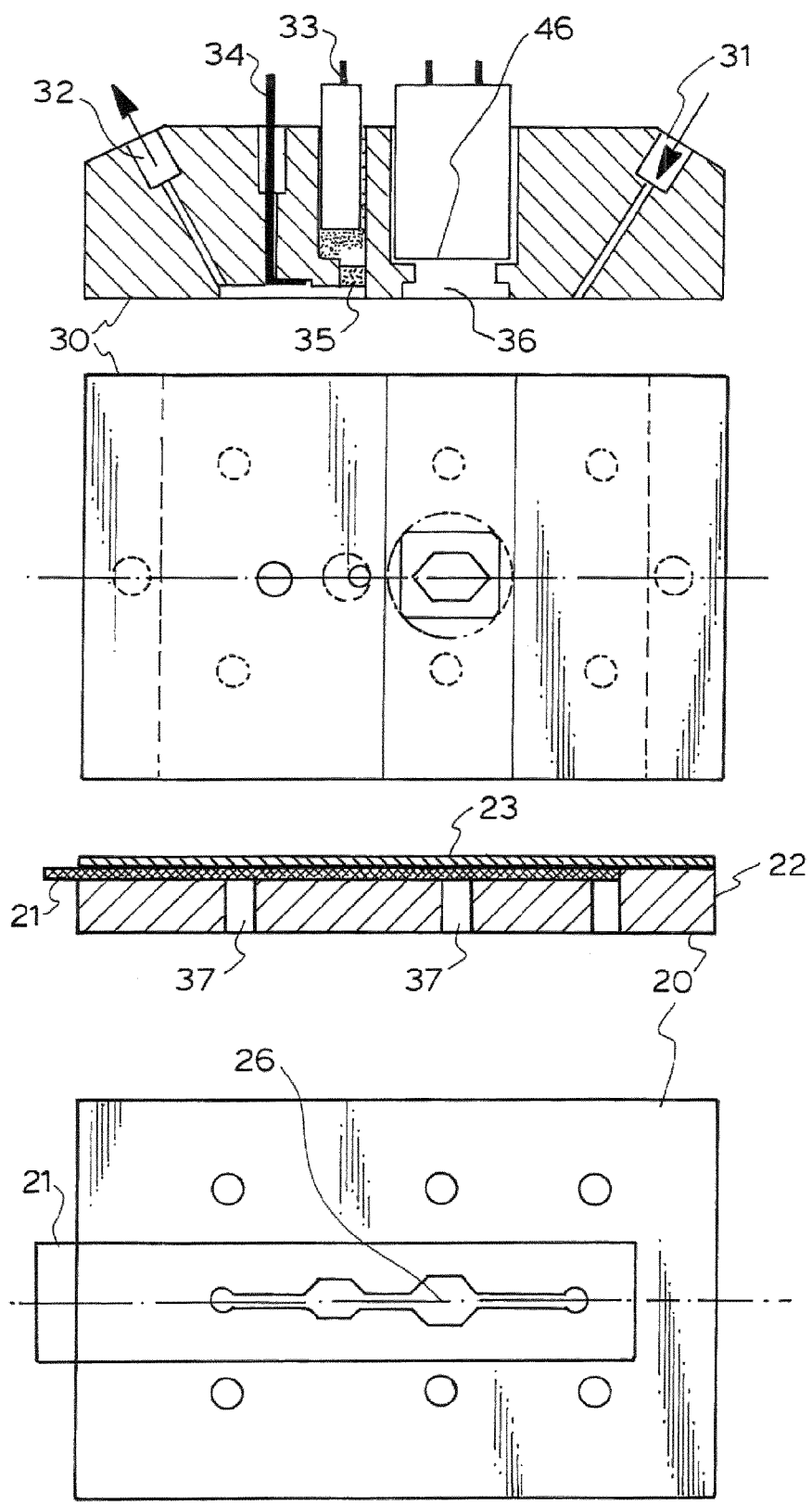
Figure 20:
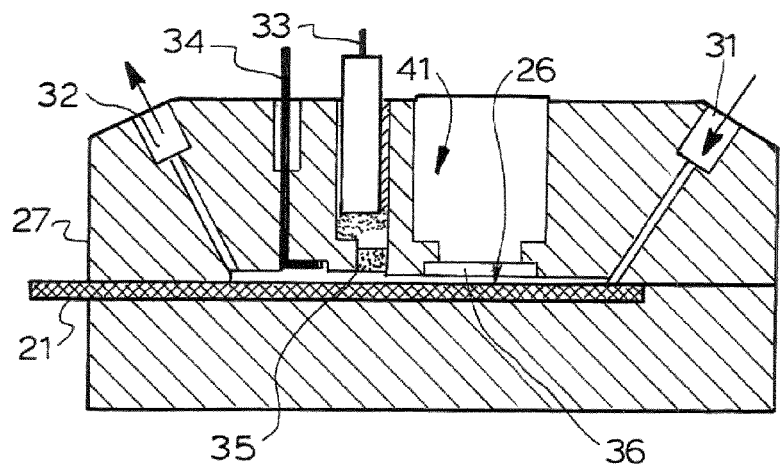
Figure 21:
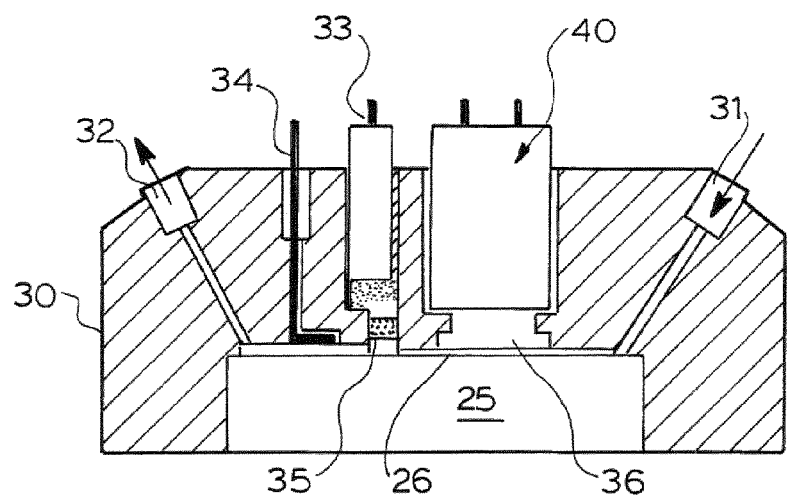
Figure 21:
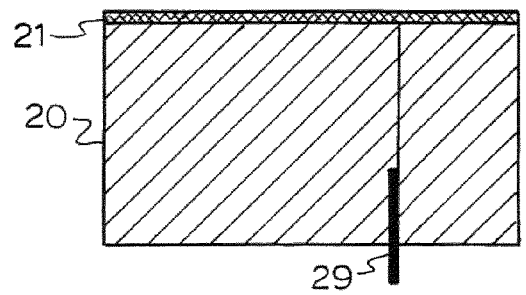
Figure 22:
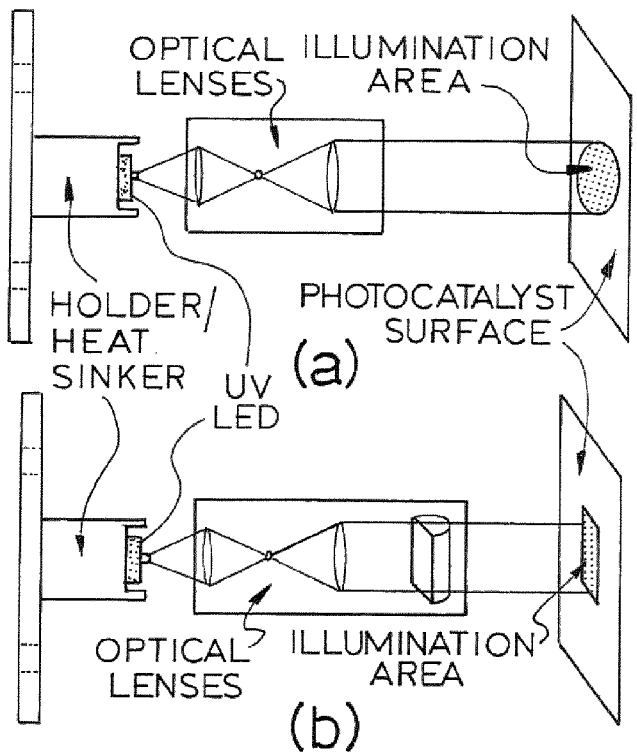
Figure 23:
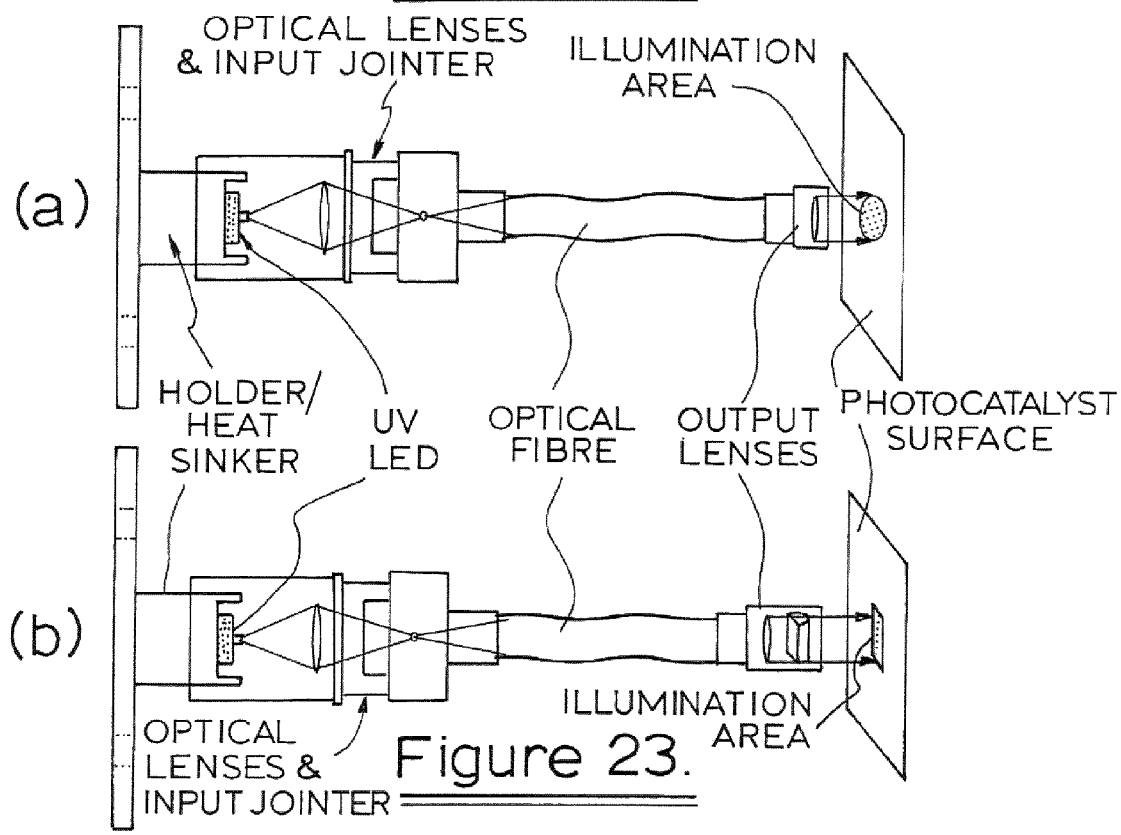
Figure 24:
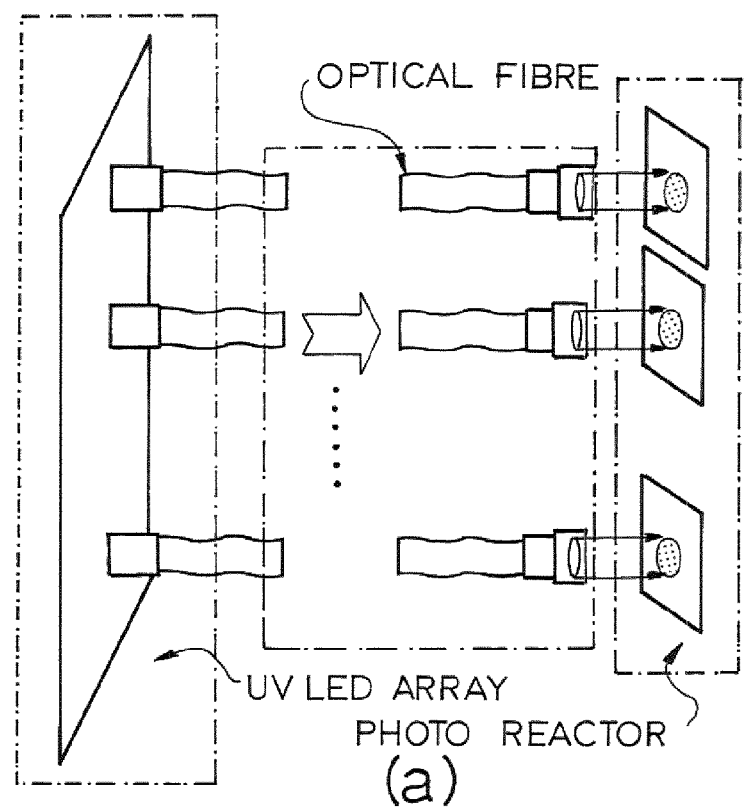
Figure 24:
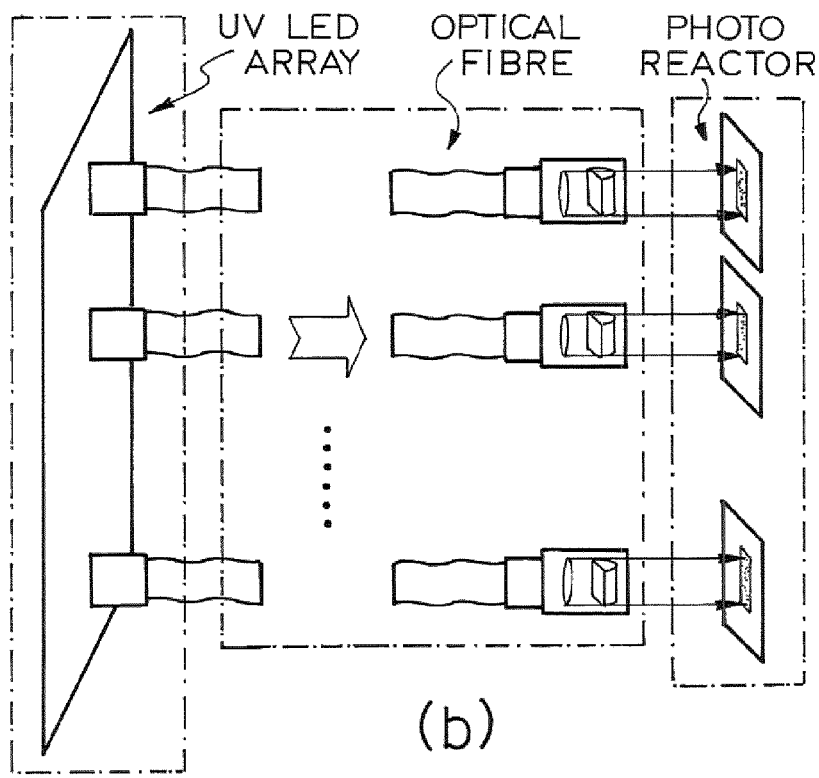
Figure 25:
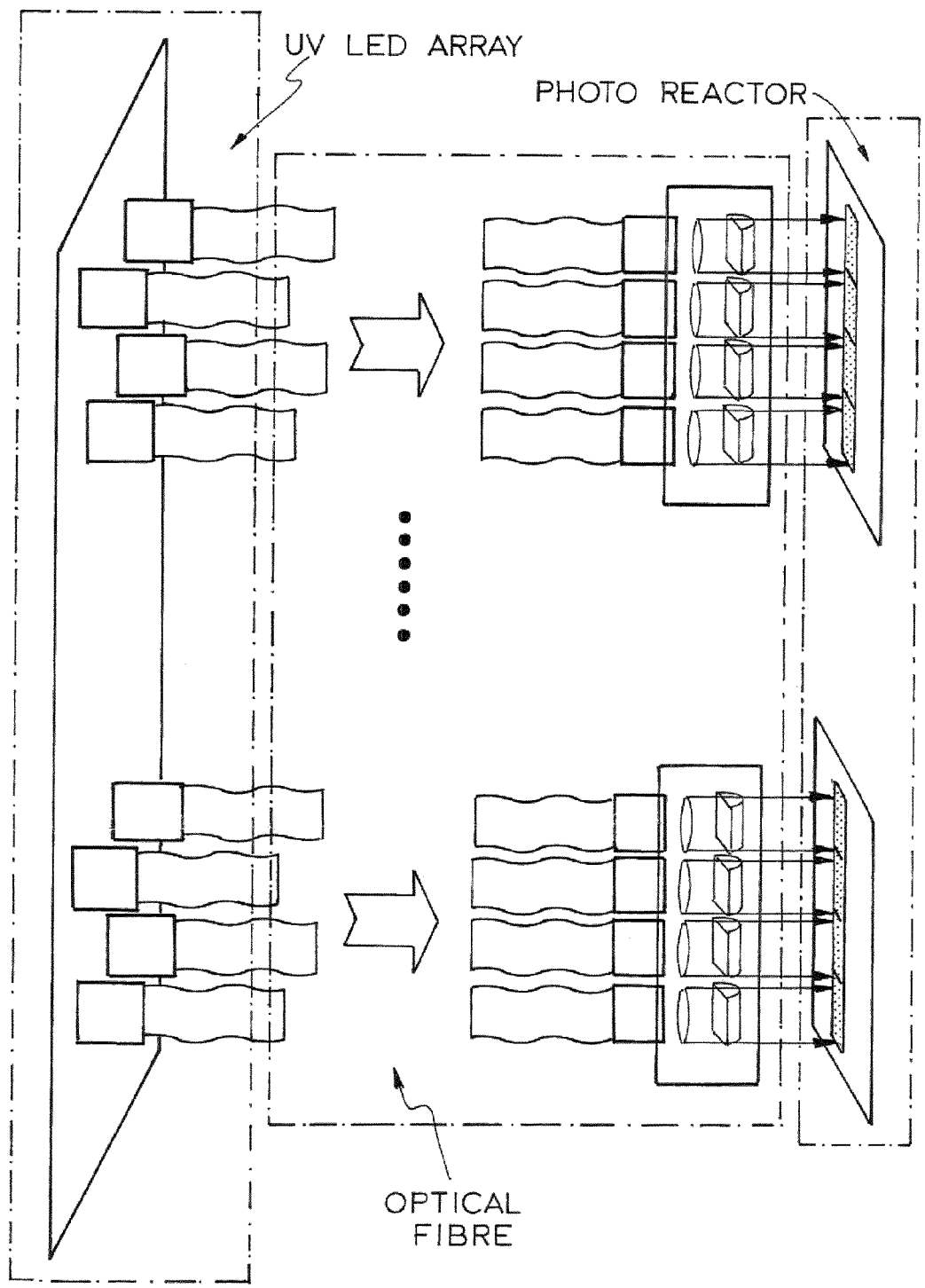

FIG. 16 Pearson correlation between PECOD and conventional COD method (dichromate);

FIG. 17 Schematic diagram of field analyser of a preferred embodiment of this invention;

FIG. 18 Schematic diagram of a cell with a disposable electrode holder and working electrode according to another embodiment;

FIG. 19 Schematic diagram of a cell with a disposable cell portion containing the working electrode;

FIG. 20 Schematic diagram of a disposable cell with a recess for the UV source;

FIG. 21 Schematic diagram of a cell with a disposable electrode holder and working electrode according to a further embodiment;

FIG. 22 Schematic diagram of directivity regulators;

FIG. 23 Schematic diagram of optical fibre directivity regulators;

FIG. 24 Schematic diagram of multi channel optical fibre directivity regulative array;

FIG. 25 Schematic diagram of multi channel optical fibre directivity regulative arrays for long narrow out put.

DETAILED DESCRIPTION OF THE INVENTION

The preferred assay method of the invention takes advantage of the highly efficient photochemical properties of $TiO_2$ nanoparticulate film electrodes to develop a new, rapid, cost-effective assay for the determination of aggregate organic properties, such as oxygen demand and in particular COD.

This embodiment is directed to a method of determining chemical oxygen demand of water samples utilising a nanoparticulate $TiO_2$ film electrode. It will be appreciated by the person skilled in the art that other nanoparticulate semiconductive film electrode may be utilised in the method without departing from the essence of the invention.

The assay method of the invention allows for easy quantification of electron transfer at a $TiO_2$ nanoparticle film electrode during photocatalytic oxidative degradation of organic material. This approach overcomes many of the current problems with existing oxygen demand techniques.

Figure 1:
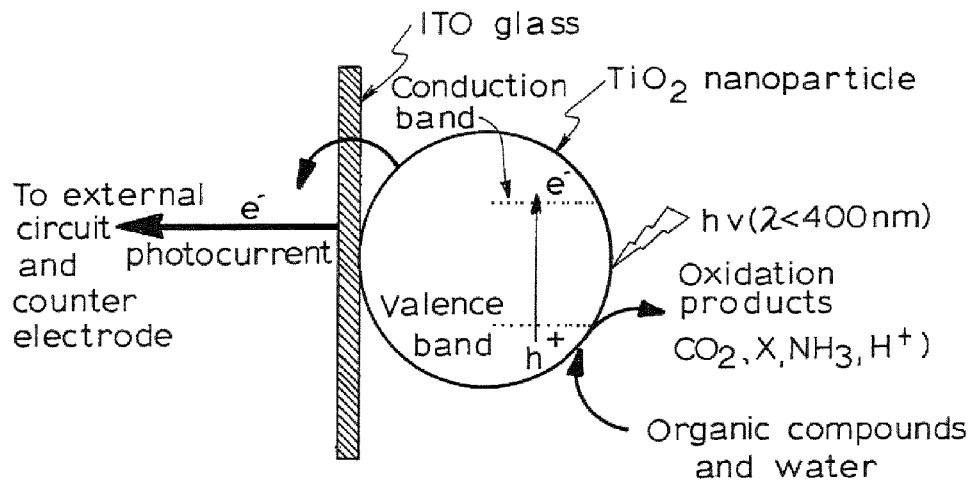
FIG. 1. is a schematic illustration of the analytical signal generation for use in the chemical oxygen demand method of this invention.

The photocatalytic oxidation approach for COD determination utilizes $TiO_2$ particles as photocatalyst to replace the traditional oxidizing agent, e.g. dichromate and permanganate. Illumination of $TiO_2$, with photons whose energy is equal to or greater than the band-gap energy, will result in promotion of an electron from the valence band to the conduction band (see FIG. 1). This promotes an electron ($e^-$) to the conduction band and leaves a positive photohole ($h^+$) in the valence band. The photohole is one of the most powerful oxidizers due to its high bandgap potential (+3.2V for anatase). The photocatalysis can lead to stoichiometric mineralization of organic compounds due to the strong oxidation power of photoholes.

Mathematical Derivation

The method of determining chemical oxygen demand of water samples, according to the invention, utilises photoelectrochemical current (or charge) generated from photoelectrochemical oxidative degradation of organic compounds as an analytical signal.

The photocatalytic degradation efficiency at $TiO_2$ depends on the degree of recombination of photoelectrons and holes. With traditional $TiO_2$ photocatalysis systems, this relies on how fast the photoelectrons and holes are consumed by the adsorbed species.

A $TiO_2$ nanoparticulate film electrode is used as the working electrode in a three-electrode photoelectrochemical cell. By applying an appropriate potential bias to the working electrode, it becomes more favourable for the photoelectron to be transferred to the working electrode rather than to the adsorbed $O_2$. The photoelectrons are subsequently forced to pass into the external circuit and to the counter electrode, where the reduction of oxygen (or other species) takes place. The photocurrent (or charge) is monitored and gives a direct measure of the oxidation of organic compounds. In effect the assay shunts photoelectrons through the external circuit to quantify the extent of oxidative degradation.

Separation of the oxidative and reductive half-reactions (Eqn.s 1 and 2, below) by imposing the electrochemical potential suppresses the recombination of photoelectrons and holes. As a result, the degradation efficiency is enhanced. In addition it has been found that the rate of degradation of organic materials is independent of $O_2$ concentration as the rate of reduction at the counter electrode will never be the rate-limiting step of the overall degradation process. Thus overcoming the prior art problem of oxygen reduction being a rate-limiting step in the photooxidation of organic material.

i.e. $h_{vb}^+ + R—H_{(ads)} \rightarrow R^*_{(ads)} + H$, or $h_{vb}^+ + H_2O_{(ads)} \rightarrow OH^*_{(ads)} + H^+$ (1)

i.e. $2e_{cb}^- + 2H^+ + O_{2(ads)} \rightarrow H_2O_2$ (2)

or $6e_{cb}^- + \frac{3}{2}O_{2(ads)} + 6H^+ \rightarrow 3H_2O$

Quantification of Analytical Signal

The photoelectrochemical system described above can be used for two different degradation models—exhaustive and non-exhaustive degradation. With exhaustive degradation, 100% of the organic analyte in the sample is consumed; with non-exhaustive degradation, only a small fraction of available analyte is consumed and its concentration in the bulk solution remains essentially unchanged. The former is analogous to bulk electrolysis in which all of the analyte is electrolysed and Faraday's Law is used to quantify the concentration by measuring the charge passed; the latter is analogous to amperometric methods where the analytical signal (i.e. current) is dependent on the rate of mass transfer to the electrode surface. In our case, however, the charge/current produced is the result of photoelectrochemical processes.

When the exhaustive degradation model is employed, the charge (Q) can be measured by the integration of photocurrent within the degradation period. The analytical principle can be established using Faraday's Law:

$$Q = \int i dt = nFN = nFVC \quad (3)$$

where:

N=number of moles of analyte in the sample, n=number of electrons transferred during the photo-electrochemical degradation, F=Faraday constant, V=sample volume; and C=analyte concentration.

Since $TiO_2$ oxidises organic compounds to the fully oxidised form of carbon (i.e. $CO_2$), the value n for a given compound will be a constant. Eqn 3 can therefore be used to quantify the analyte concentration.

In principal, analytically useful photocurrents (or charge) can be obtained from any photo-electrochemically degradable species. The $TiO_2$ system proposed is capable of oxidising nearly any organic or low redox state inorganic species (e.g. $Fe^{2+}$, $Cl^-$, $NH_4^+$, $NO_2^-$). In this respect, the proposed system can be employed as a "universal" detector capable of detecting any compounds that can be photoelectrochemically oxidised at a $TiO_2$ electrode. In combination with an appropriate separation system (e.g. HPLC), the concentration of individual analytes can be determined.

In terms of general water quality issues and pollution control, the effect and quantification of aggregate mixtures of organics (such as in COD or BOD analysis) are often more important than the analysis of single species. The proposed photoelectrochemical system is capable of determining such aggregate properties by summing the charge measured from individual photo-electrochemically degradable compounds within a mixture (Eqn 4).

$$Q = \int i dt = FV \sum_{i=1}^{m} n_i C_i \quad (4)$$

The measured charge, Q, is simply the total amount of electron transfer that results from the degradation of all compounds in the sample. Given that oxidation by $O_2$ can be represented as:

$$O_2 + 4H^+ + 4e^- \rightarrow 2H_2O \quad (5)$$

where one oxygen molecule is equivalent to 4 electrons, the measured Q value can be easily converted into an equivalent $O_2$ concentration (or oxygen demand) value:

$$\text{Equivalent Oxygen Concentration (mole/L)} = \frac{Q}{4FV} \quad (6)$$

For exhaustive degradation, the equivalent COD value of the sample can therefore be represented as:

$$COD(\text{mg/L of } O_2) = \frac{Q}{4FV} \times 32000 \quad (7)$$

In the case of non-exhaustive degradation, the quantitative relationship between the photocurrent and the concentration of the analyte can be developed using a well-known semi-empirical treatment of Steady-State Mass Transfer [A. J. Bard and L. R. Faulkner, *Electrochemical Methods-Fundamental and Applications*. John Wiley & Sons, Inc. New York. 2001]. Under conditions of forced convection, the rate of mass transfer (dN/dt) to an electrode is directly proportional to the concentration gradient at the electrode surface.

$$\left(\frac{dN}{dt}\right) = k[C_b - C_s(x=0)] \quad (8)$$

where,
- $C_b$=concentration of analyte in the bulk solution;
- $C_s$=concentration of analyte at the electrode surface;
- k=mass-transfer coefficient [A. J. Bard and L. R. Faulkner, *Electrochemical Methods-Fundamental and Applications*. John Wiley & Sons, Inc. New York. 2001] which is $=D/\delta$, where D=diffusion coefficient and $\delta$=thickness of stagnant layer.

When sufficient photo intensity and adequate potential bias are employed, and the overall process is controlled by mass transfer, then, $C_s(x=0) \ll C_b$, so that $[C_b - C_s(x=0)] \approx C_b$. The maximum rate of mass transfer, $(dN/dt)_l$ is achieved and the rate of overall reaction equals:

$$\text{Rate} = \left(\frac{dN}{dt}\right)_l = kC_b \quad (9)$$

If we again assume that after photochemical oxidation the analyte is fully oxidised, then the number of electrons transferred (n) during photoelectrochemical degradation is a constant, for a given analyte. The limiting photocurrent ($i_l$) can, therefore, be used to represent the rate of reaction:

$$i_l = nFA\left(\frac{dN}{dt}\right)_l = nFAkC_b \quad (10)$$

where A=active electrode area.

The development of equation 10, by the current inventors, leads to definition of the quantitative relationship between the limiting photocurrent and the concentration of analyte and can be regarded as the principle of analysis.

This analytical principle can again be applied to determine concentrations of individual analytes (and serve as a "universal" detection system) or to aggregate mixtures of organics (to determine properties such as COD). Whilst formula 10 above may allow for the general determination of analyte concentration, it is the application of the findings from formula (10) to the determination of COD that assists in addressing one or more of the disadvantages in the prior art methodologies. Standard analytical and mathematical techniques may be used to calculate the COD of a sample from the limiting photocurrent measured in a photoelectrochemical cell utilising a nanoparticulate $TiO_2$ semiconductive electrode in the manner described in more detail below.

Method of Determining Cod

Formation of $TiO_2$ Electrode

A) Synthesis of $TiO_2$ Colloid

A1) A mixture of 12.5 ml titanium butoxide and 4 ml isopropyl alcohol was added, drop-wise, to 150 ml 0.1 M nitric acid solution under vigorous stirring at room temperature. After the hydrolysis the slurry was heated to 80° C. and stirred for 8 h to achieve peptization. The colloid is then filtered to remove the nonpeptized agglomerates. For better crystallinity of the nanoparticles, the colloid was hydrothermally treated in an autoclave at 200° C. for 12 h. During the autoclaving sedimentation occurred, and the particles were redispersed by sonication. The particle size is in the range of 8 to 10 nm as characterised by transmission electron microscopy (TEM). Water was used to adjust the final solid concentration to ca. 6% (wt) and carbowax 20M (Merck) was added to the colloid in a proportion of 1-50% of the $TiO_2$ weight. The colloid thus obtained was used for the preparation $TiO_2$ nanoporous film electrode.

A2) A 16.0 cm³ of isopropanol (Aldrich, AR grade) and 50.0 cm³ of titanium butoxide (Aldrich, AR grade) were accurately measured into a 150 cm³ dropping funnel. The resulting solution was added over 15 minutes with vigorous stirring to 600 cm³ of ultrapure deionized water (18.2 MΩ cm) in a conical flask. On the completion of the addition, 4.0 cm³ of 70% nitric acid (AR grade) was added into the solution as a peptizing agent. The solution was immersed in a hot water bath, heated to 80° C. and stirred continuously for 10 hours. Approximately 400 cm³ of a white colloidal solution remained and was stored in a dark glass vessel for use. The sizes of the $TiO_2$ synthesised according to this procedure were in a range of 8 to 10 nm.

The colloidal $TiO_2$ prepared above was placed in an autoclave reactor (Parr bomb) and autoclaved for 12 hours at 200° C. before concentrating on a rotary evaporator to 8% (w/w), resulting in a white semi-viscous colloidal solution. 40% $TiO_2$ weight equivalent (e.g. 1.6 g in 50.0 cm³ of 8% colloidal solution) of Carbowax 6,000 was added to the solution and stirred for approximately 20 minutes.

B) Immobilisation of $TiO_2$ Film on ITO Glass

B1) ITO (tin doped iridium oxide) conducting glass slides were used as the substrate for immobilisation of $TiO_2$ particles. To get a clean surface the ITO glass slide was pretreated by washing in turn with detergent, water, and ethanol. After the pretreatment the ITO slide was dip-coated in the above colloidal solution from A1, above. The coated slides were then calcined in a muffle furnace in air at 500 to 800° C. for 0.5 h to 30 h. The particle size of $TiO_2$ on the films characterised by x-ray diffraction and scanning electron microscopy (SEM) is in the range of 10 nm to 100 nm and the rutile/anatase phase ratio is in the range of 0.1 to 50%.

B2) $TiO_2$ films were prepared in a clean room environment to minimize contamination from dust particles. $TiO_2$ colloidal coating solution, from A2 above, was stirred vigorously and subjected to the ultrasonic treatment for 20 minutes prior to a dip coating process to achieve a consistent, reproducible homogeneous mixture. The ITO slide (conducting glass) was used as the electrode substrate and was pre-treated by washing in turn with detergent, water, acetone and water, and finally dried by pure nitrogen. After pre-treatment, the ITO slide was dip-coated with the $TiO_2$ colloidal coating solution using a dip coating equipment with drawing speeds of 0.5-1.5 cm/min. The coated electrodes were then calcined in a muffle furnace at 450° C. for 30 minutes in air. The nanoporous $TiO_2$ films with 1 μm thickness and anatase crystalline structure were obtained. The films with different thicknesses can be prepared by controlling the withdrawing speed during the dip coating.

C) General Setup of the Photoelectrochemical System

Figure 2:
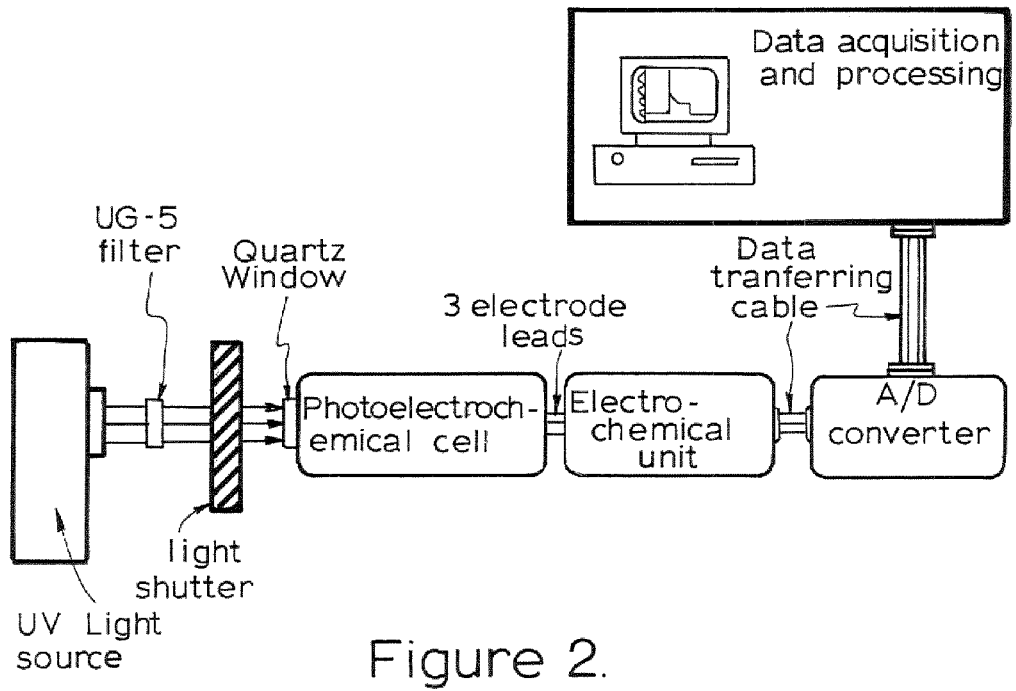
FIG. 2 Schematic of the instrumentation of photoelectrochemical detection system.

FIG. 2 shows the schematic of the instrumental set up of the photoelectrochemical detection system. Illumination was carried out using a 150 W xenon arc lamp light source with focusing lenses (HF-200W-95, Beijing Optical Instruments). To avoid the sample solution being heated-up by infrared light, the light beam was passed an UV-band pass filter (UG 5, Avotronics Pty, Limited) prior to illumination of the electrode surface. A light shutter was used to control the ON and OFF of the illumination.

Generally, photoelectrochemical experiments were performed in a three-electrode electrochemical cell with a quartz window for illumination. The $TiO_2$ film electrode was installed in an electrode holder with ca. 0.65 cm² left unsealed to be exposed to the solution for illumination and photoelectrochemical reaction. A saturated Ag/AgCl electrode and a platinum mesh were used as the reference and counter electrodes respectively. A voltammograph (CV-27, BAS) was used for application of potential bias in steady state photocurrent measurements. Potential and current signals were recorded using a Macintosh computer (7220/200) coupled to a Maclab 400 interface (AD Instruments).

D) The Measurement Procedures:

D1) Exhaustive Degradation Conditions

Step 1: Once the system is set up (see FIG. 2-6), the supporting electrolyte solution was pumped through the photoelectrochemical cell (a thin layer cell). A bias potential of +0.20 V vs a Ag/AgCl reference electrode was applied. Once the stable baseline was obtained, the pump was stopped. The photo shutter was then switched on to allow UV radiation to reach the electrode. The photocatalytic reaction occurred and the background current-time profile can be measured (see FIG. 10 curve (a)). The background current ($i_{Background}$) was resulted from the photocatalytic oxidation of water. Integrating $i_{Background}$ with time we can obtain the background charge, $Q_{Background}$.

Step 2: After the measurement of $Q_{Background}$, the photo shutter was switched off and a 5 μl to 200 μl of sample solution with appropriate concentration was injected into the photoelectrochemical cell (It is to note that the sample volume injected is depending the volume of the cell and if the concentration of organics in the sample was too high then an appropriate dilution may be required prior the injection). Once the sample injection was completed, the pump was stopped and the photo shutter was switched on. The Current-time profile was measured (see FIG. 10 curve (b)). The current obtained here is the total photocurrent ($i_{Total}$) that resulted from the oxidation of water and organics. Same to the above, by integrating $i_{Total}$ with time we have the total charge, $Q_{Total}$.

Step 3: Since the background charge, $Q_{Background}$, is a constant for the given experimental conditions and the total charge, $Q_{Total}$, varied with the concentration of the sample, therefore, the net charge, $Q_{net}$ (the shaded area shown in FIG. 10) that resulted from the oxidation of organics can be obtained by subtracting the background charge from the total charge, that is:

$$Q_{net} = Q_{Total} - Q_{Background}$$

The COD value of the sample can then be calculated according to the equation (7) since in the equation, $$COD(mg/L \text{ of } O_2) = \frac{Q_{net}}{4FV} \times 32000 \qquad (7)$$

F is a constant and V is known sample volume.

Repeating steps 2 and 3 to analysis next sample.

D2) Non-Exhaustive Degradation Conditions

The system set up was same as described above (see FIG. 2-6) except that a normal flow-through cell was employed to replace the thin layer cell. The measurement can be done by using a standard addition method or by other calibration means.

Figure 7:
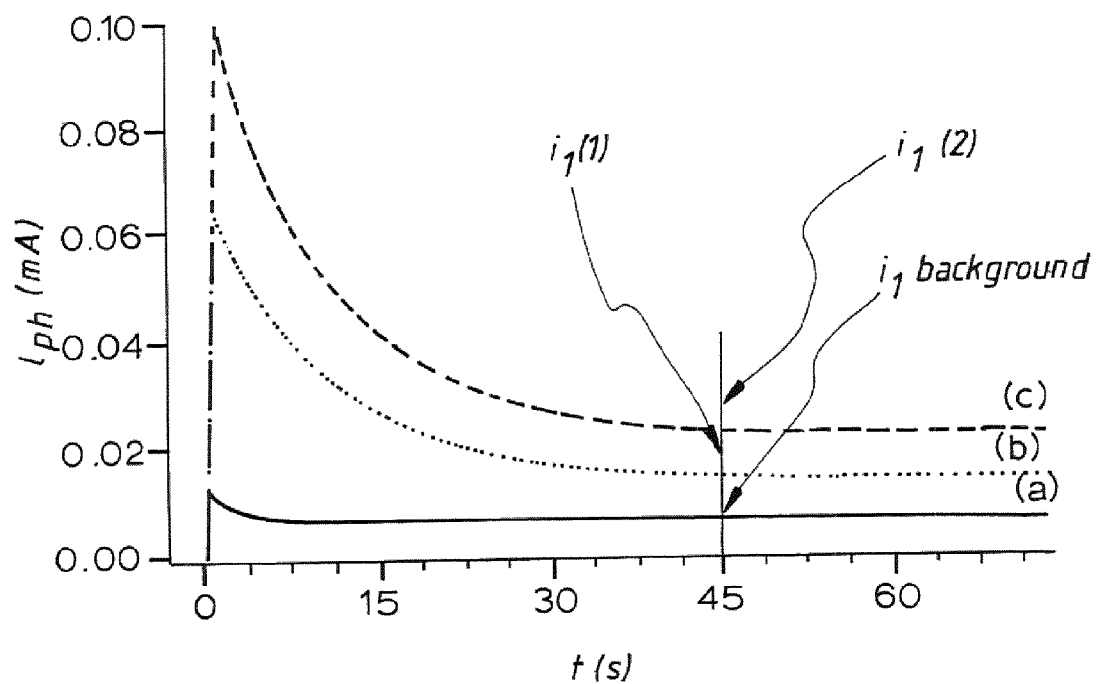
FIG. 7. Graphical representation of non-exhaustive degradation, photocurrent/time profiles of supporting electrolyte, sample and standard solutions.

Step 1: The supporting electrolyte solution was pumped through the photoelectrochemical cell (a normal flow-through cell with cell volume of 0.5 to 2.5 ml). A bias potential of +0.20 V vs a Ag/AgCl reference electrode was applied. Once the stable baseline was obtained, the pump was stopped. The photo shutter was then switched on to allow UV radiation to reach the electrode. The photocatalytic reaction occurred and the background current-time profile can be recorded (see FIG. 7 curve (a)). The background current ($i_{background}$) was resulted from the photocatalytic oxidation of water.

Step 2: After the measurement of $i_{background}$, the photo shutter was switched off and a 0.5 ml to 2.5 ml of sample solution with appropriate concentration was injected into the photoelectrochemical cell (It is to note that the sample volume injected is depending the volume of the cell and if the concentration of organics in the sample was too high then an appropriate dilution may be required prior the injection). Once the sample injection was completed, the pump was stopped and the photo shutter was switched on. The Current-time profile was recorded (see FIG. 7 curve (b)). The current obtained here is the total photocurrent ($i_{total}$) that resulted from the oxidation of water and organics.

Step 3: Once the measurement of $i_{total}$ was completed, the photo shutter was switched off and a 0.5 ml to 2.5 ml of sample solution containing an appropriate concentration of standard was injected into the photoelectrochemical cell. Once the sample injection was completed, the pump was stopped and the photo shutter was switched on. The current-time profile was recorded (see FIG. 7 curve (c)). The current obtained here is the photocurrent ($i_{standard}$) that resulted from the oxidation of water and the organics in both original sample and the added standard.

Step 4: After the above measurements, the COD of the sample can be calculated according to the equation (10).

Figure 5:
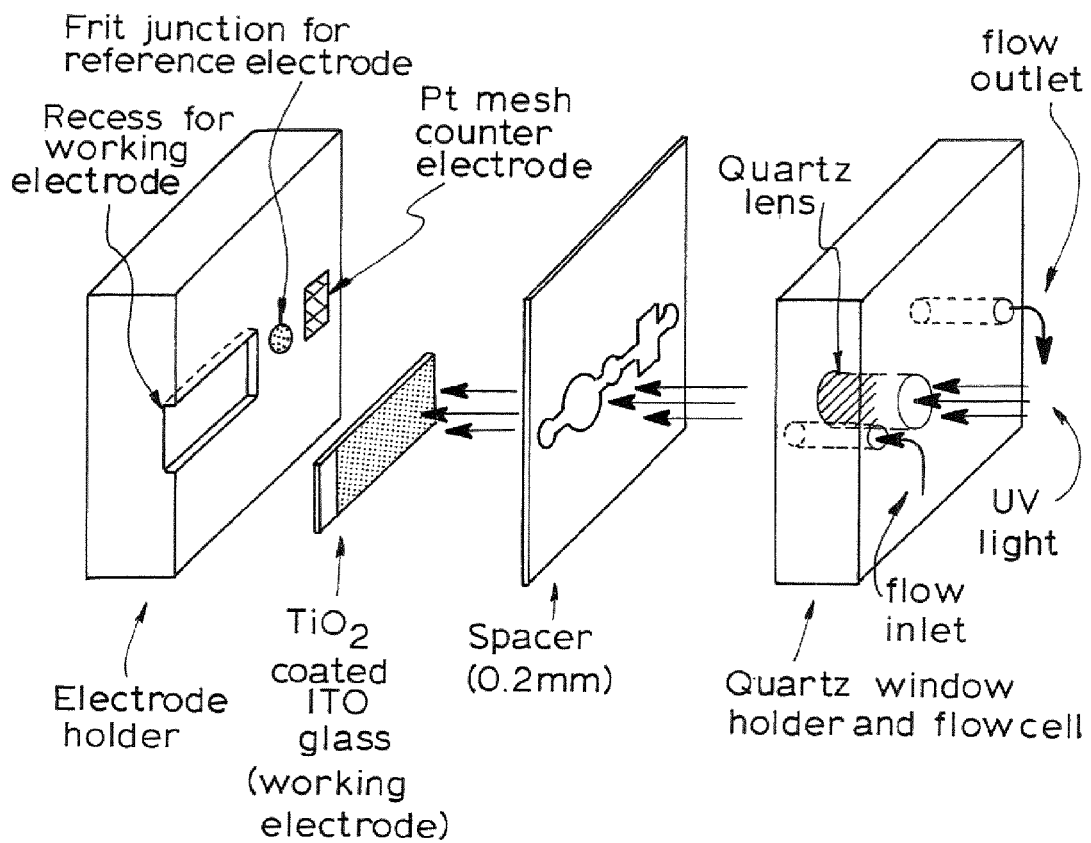
FIG. 5 Schematic diagram of the thin-layer photoelectrochemical flow cell.

The limiting current for each case ($i_{l\ background}$, $i_l(1)$ and $i_l(2)$), can be obtained by measuring the steady current value from each curve, for example, at 45 s (see FIG. 5). The net limiting photocurrents for the sample solution ($i_l(1)$) and for the sample with added standard ($i_l(2)$) can then be calculated.

Net limiting photocurrents (or current) for the sample solution:

$$i_{l\,sample} = i_l(1) - i_{l\,background}$$

Net limiting photocurrents (or current) for the sample with standard:

$$i_{l\,standard} = i_l(2) - i_{l\,background}$$

According to equation (10), above, we have:

$$i_{lsample} = nFAk[COD]_{sample} = K[COD]_{sample}$$

$$i_{l\,standard} = nFAk\{[COD]_{sample} + [COD]_{standard}\} = K\{[COD]_{sample} + [COD]_{standard}\}$$

where $K = nFAk$ is a constant for a given experimental condition.

The COD value of the sample solution:

$$[COD]_{sample} = \frac{i_{lsample}}{i_{lstandard} - i_{lsample}} \times [COD]_{standard}$$

Repeat the steps 2 to 4 for the next sample.

It will be appreciated by the person skilled in the art that the necessary computations set out above may be automated with the appropriate programming of a personal computer.

There are a few operational modes with different photoelectrochemical reactor designs (i.e. online thin-layer flow cell, and batch cell) that utilise the assay methodology and are demonstrated by following examples.

Example 1

Quantification of COD Using Photocurrent

Figure 3:
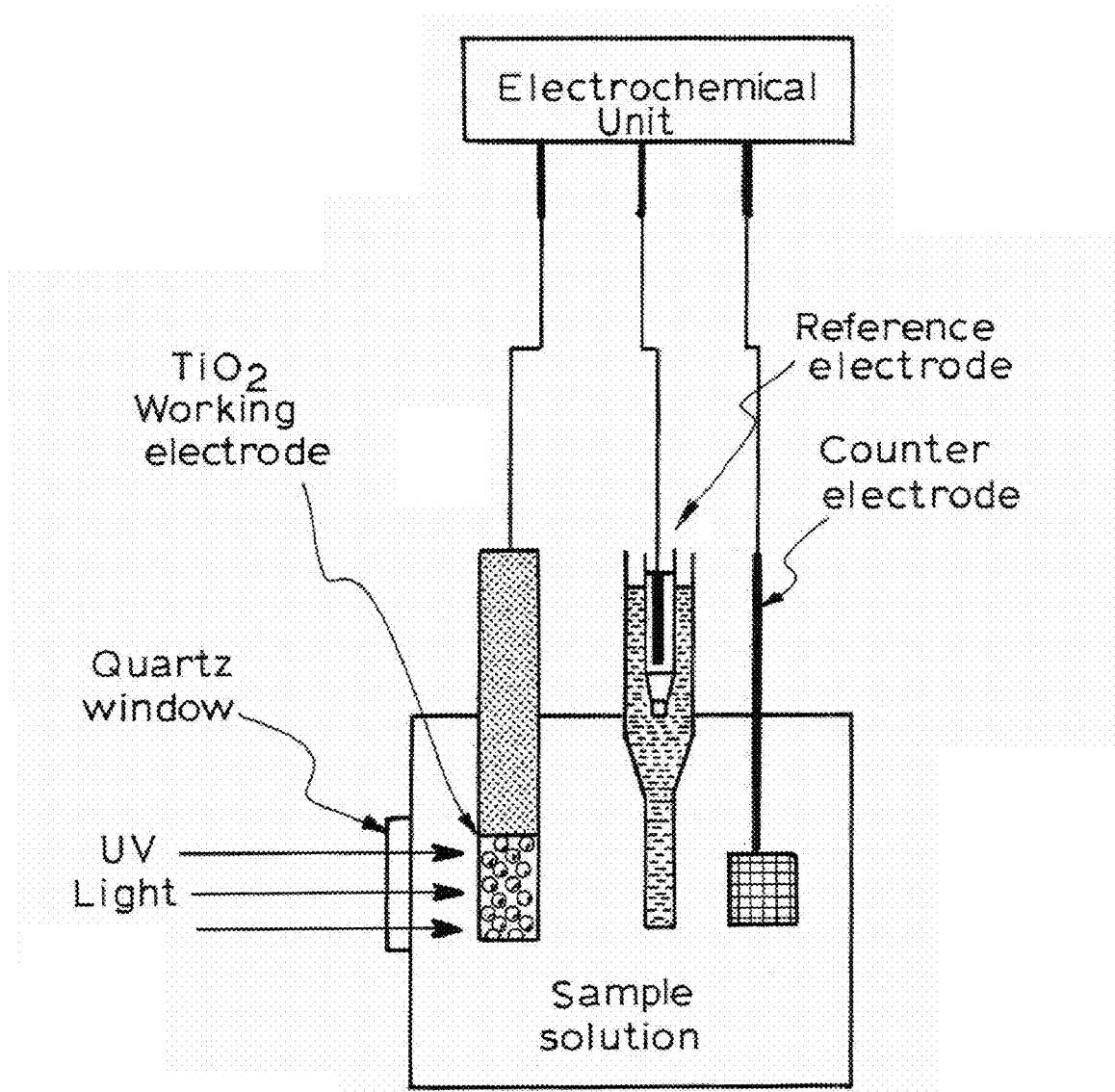
FIG. 3. Schematic diagram of the photoelectrochemical batch (stationary) cell of this invention.

The photoelectrochemical experiment was performed in a three-electrode electrochemical batch cell with a quartz window for illumination as shown in FIG. 3 The $TiO_2$ film electrode was placed in an electrode holder with ca. 0.65 $cm^2$ left unsealed to be exposed to the solution for illumination and photoelectrochemical reaction. 0.1 M $NaNO_3$ solution was used as the supporting electrolyte. A potential bias of +0.2V was applied at the electrode and limiting photocurrents were obtained for different organic compound concentrations when the current reached steady state. The limiting photocurrent differences between samples and the blank 0.1 M $NaNO_3$ solution were taken as analytical signals, which are directly linear to organic compound concentrations within diffusion control. A linear relationship between the analytical signal and COD value was then acquired after the concentration was converted into COD value.

Example 2

Quantification of COD Using Charges

Figure 4:
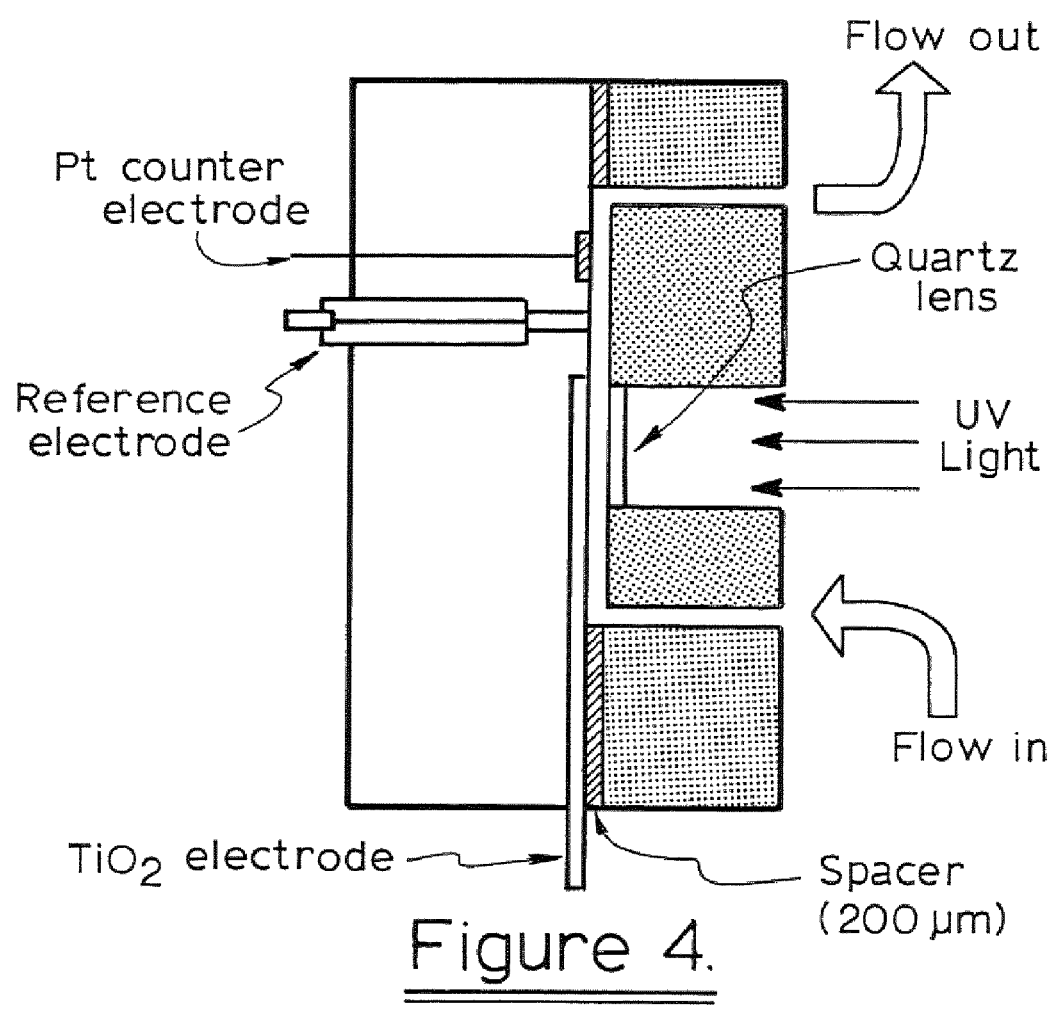
FIG. 4. is a schematic cross section of a thin-layer photoelectrochemical flow cell according to this invention.

In this case the experiment was carried out in a thin-layer photoelectrochemical cell as shown in FIGS. 4 and 5. A potential bias of +0.20V was applied and 2M $NaNO_3$ was used as supporting electrolyte. Firstly, a 2M $NaNO_3$ electrolyte solution was injected into the thin-layer photoelectrochemical cell with a syringe and a blank transient photoelectrolysis was run as a blank sample. The photocurrent-time profile was recorded until the photocurrent reached steady state. Then samples containing organic compounds and 2M $NaNO_3$ were injected into the thin-layer cell and the sample transient photoelectrolysis was run. The photocurrent-time profile was recorded until the photocurrent attained steady state, indicating the organic compounds have been exhaustively photoelectrolysed. The cell was washed with supporting electrolyte solution between each sample injection. Integrating the photocurrent-time profile gives the photocatalytic oxidation charge. The charge difference between sample and blank transient photoelectrolysis was taken as the analytical signal, which is directly proportional to the COD value. COD value was then determined.

Example 3

Quantification of COD Using Charges and FIA

Figure 6:
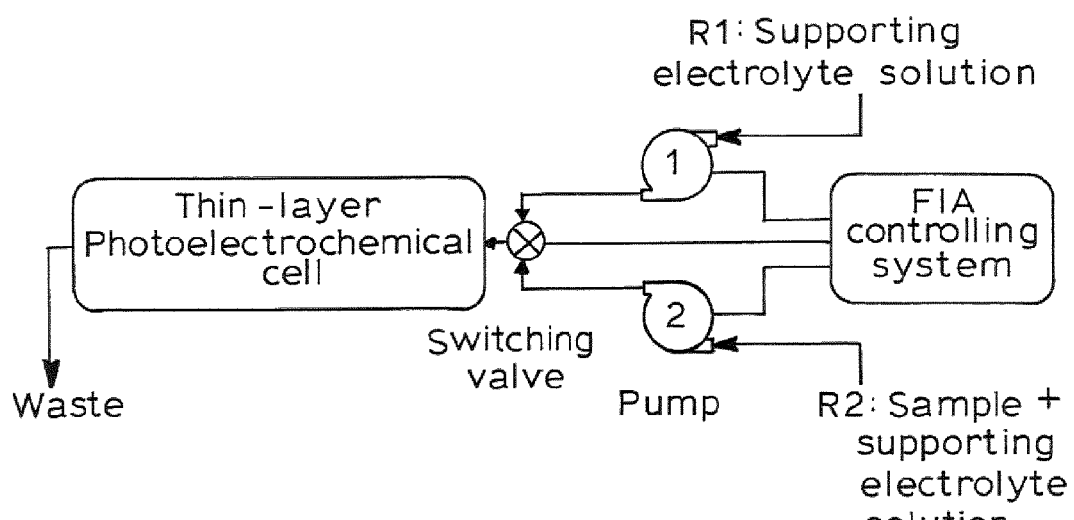
FIG. 6. FIA Manifolds for sample and supporting electrolyte injection in an automatic COD photoelectrochemical detection system.
Figure 6:
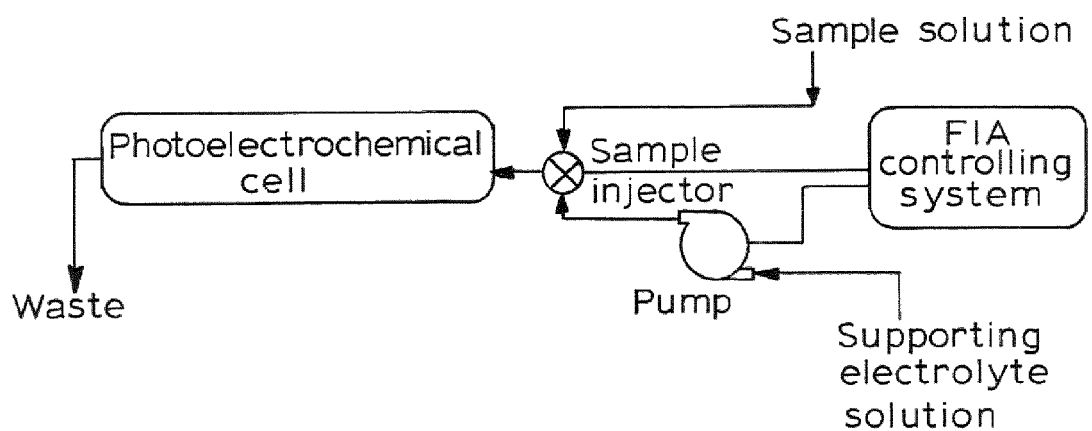

Besides the use of the thin-layer photoelectrochemical cell, a flow injection analysis (FIA) system was incorporated into the COD determination. With the combination of FIA, automatic COD determination was realised. In this case, the injection of samples and cell cleaning was controlled by a FIA controlling system as shown in FIG. 6 (*a*). Pump 1 achieves the blank sample (R1) injection and cell cleaning while Pump 2 does the sample injection (R2). A potential bias of +0.20V was applied and 2M $NaNO_3$ was used as supporting electrolyte (blank sample). Firstly, a 2M $NaNO_3$ electrolyte solution was pumped into the thin-layer photoelectrochemical cell by Pump 1 and a blank transient photoelectrolysis was run as a blank sample. The photocurrent-time profile was recorded until the photocurrent reached steady state. Then samples containing organic compounds and 2M $NaNO_3$ were pumped into the thin-layer cell by Pump 2 and the sample transient photoelectrolysis was run. The photocurrent-time profile was recorded until the photocurrent attained steady state, indicating the organic compounds have been exhaustively photoelectrolysed. The cell was washed with supporting electrolyte solution by Pump 1 between each sample. Integrating the photocurrent-time profile gives the photocatalytic oxidation charge. The charge difference between sample and blank transient photoelectrolysis was taken as the analytical signal, which is directly proportional to the COD value. COD value was then determined.

Example 4

Quantification of COD Using Continuous Flow Mode

Besides the use of the thin-layer photoelectrochemical cell, a flow injection analysis (FIA) system was incorporated into the COD determination with a continuous flow operational mode. With the combination of FIA, automatic COD determination was realised. In this case, the injection of samples and cell cleaning was controlled by a FIA controlling system as shown in FIG. 6(*b*). The blank sample is continuously pumping through the cell and an injector is employed for the sample injection. A potential bias of +0.20V was applied and 2M $NaNO_3$ was used as supporting electrolyte (blank sample). Recording the photocurrent from the photocatalysis of the blank sample gives a steady baseline. An injection of sample containing organic compounds through the injector to allow the photocatalysis of sample takes place. The peak shaped photocurrent-time profile can be recorded until the photocurrent attained baseline, indicating the organic compounds have been photoelectrolysed. The next sample can then be injected for analysis. COD value of the sample can be determined by measuring either peak height or peak area (by integrating the peak photocurrent) since both peak height and peak area are directly proportional to the COD value.

Typical Experimental Results

Figure 8:
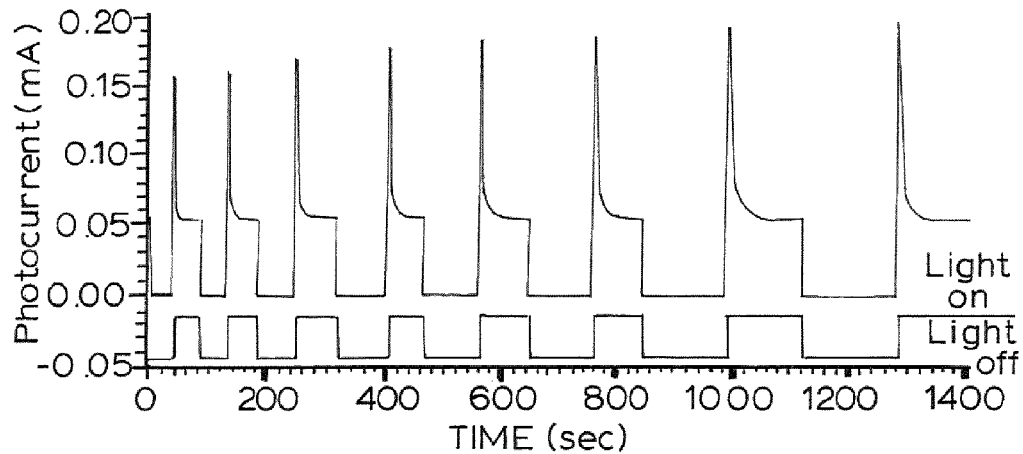
FIG. 8. Photocurrent response of a solution containing 40 µM of potassium hydrogen phthalate and 0.1 M $NaNO_3$. Photo intensity: 9.1 $mWcm^{-2}$; Applied potential bias: +0.20V vs Ag/AgCl.

FIG. 8 shows a typical photocurrent-time curve obtained from a non-exhaustive photoelectrochemical degradation process. Under a constant applied potential, when the light was switched off, the residual current (dark current) was approximately zero. Upon illumination, the current increased rapidly before decaying to a steady state value. This steady state current (limiting photocurrent) consists of two current components. One is due to mass transfer limited photoelectrochemical oxidation (degradation) of the target analyte, which is directly proportional to the concentration of the analyte. The other is due to the photoelectrochemical oxidation (decomposition) of water, which is constant at a given pH and supporting electrolyte concentration. The net limiting photocurrent, $i_l$ (resulting from analyte oxidation) can be readily obtained by subtraction of the photocurrent attributed to the oxidation of water from the total photocurrent. $i_l$ can then be used for analytical purposes (Eqn 10).

Figure 9:
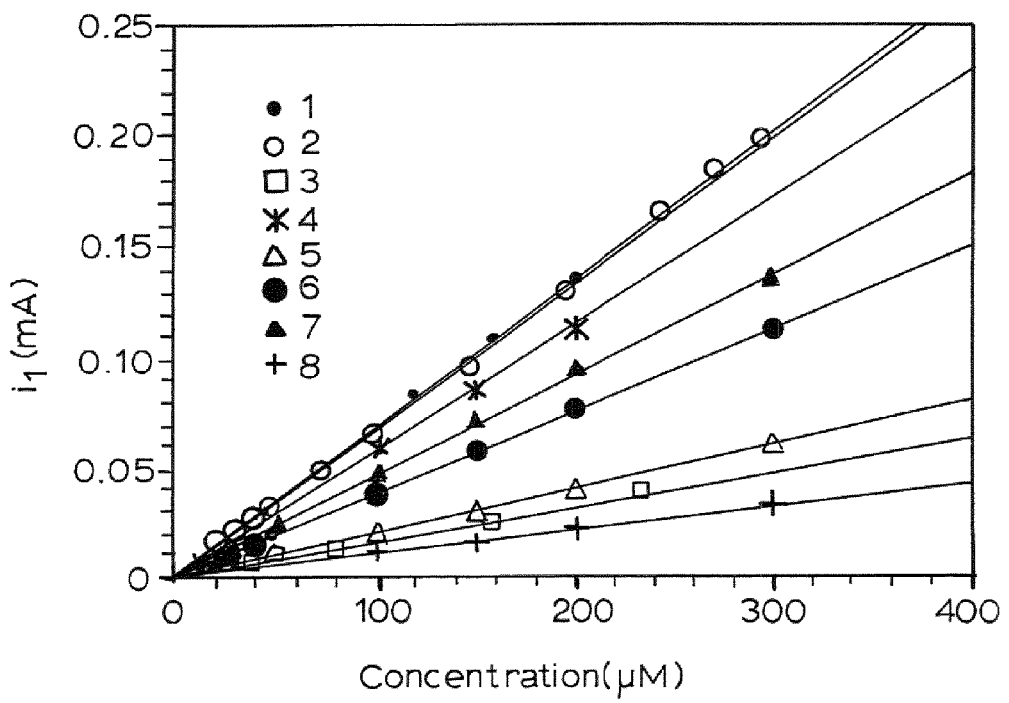
FIG. 9 $i_f$-C curves for a range of organic compounds, namely.

Preliminary results obtained from a range of organic compounds indicate that Equation 10 is applicable to all compounds investigated (see FIG. 9, in which 1=p-chlorophenol; 2=potassium hydrogen phthalate; 3=methanol; 4=d-glucose; 5=malonic acid; 6=succinic acid; 7=glutaric acid; 8=glycine). As predicted, $i_l$ was found to be directly proportional to the concentration of the organic compound. The slopes of the $i_l$-C curves (sensitivity) are determined by the mass transfer coefficient (k) and the number of electrons transferred (n) during the photoelectrochemical degradation.

The photocurrent-time profile of an exhaustive photoelectrochemical degradation process was found to be similar to that of the non-exhaustive degradation process except that a steady state photocurrent can only be achieved when all of the organic compounds were consumed. In this case, the steady state photocurrent was purely due to the oxidation of water and can be easily subtracted from the total current (FIG. 10). FIG. 10 shows the typical photocurrent-time profiles obtained from the electrodes during an exhaustive photoelectrochemical degradation process in phthalic acid and in blank electrolyte solutions. It can be seen that the photocurrent decayed with time and then reached a steady value, which was due to the oxidation of water. It is noted that the blank photocurrent obtained from the blank electrolyte solution was purely due to the oxidation of water, while the photocurrent obtained from the electrode in phthalic acid solution consists of two current components, one is due to photoelectrochemical oxidation of phthalic acid, and the other is due to the oxidation of water, which is the same as the blank photocurrent. Our experimental results showed that the blank photocurrent was essentially constant for the given set of experimental conditions.

For a given time period, the charge passed for both cases can be obtained by integration of the photocurrent and blank photocurrent. The charge difference between the two cases is the net charge, Q, due to the photoelectrochemical oxidation of phthalic acid, which is indicated as the shaded area in FIG. 10. The net charge, Q, was measured by integration of net photocurrent within the degradation period as described in FIG. 10. As predicted by Eqn. 3, Q is directly proportional to concentration (see FIG. 11). In this case, the slopes of the Q-C curves (sensitivity) were dependent only on the number of electrons transferred (n). The results in FIGS. 9 and 11 (having conformed to theory) demonstrated the possibility of further developing the proposed system into a "universal" detection system for individual analytes.

The possibility of applying the proposed method for determining aggregate properties such as COD was also tested. We chose the APHA COD standard test solution (potassium hydrogen phthalate (KHP)) and a synthetic mixture with known COD values as our test solutions. FIG. 12 shows the correlation between the experimental COD values (according to equation 7) and standard COD values. Excellent agreements between the two COD values were obtained in both cases.

Example 5

Real Waste Water Samples

Fourteen (14) different wastewater samples were collected from various industries in Queensland, Australia. After appropriate dilution, all samples were subject to the COD analysis using our method and the standard COD method. The COD values obtained from the two methods for all samples were then correlated and shown in FIG. 13. A correlation coefficient of 0.973 and slope of 0.992 were obtained. This means our method predicts the same COD value as the standard COD method. This demonstrates that our method is equivalent to the standard method in predicting the COD values.

Example 6

Determination of COD in Synthetic Samples

The use of flow injection (FIGS. 4 and 5) to determine COD in aqueous solution was first tested with synthetic samples prepared with pure organic chemicals, i.e. glucose, glutamic acid, GGA and sucrose. The time required for a single measurement was 1-2 min. FIG. 14 shows the calibration curve of the various organic compounds in terms of μM and theoretical COD concentration respectively. FIG. 14a shows that the photoelectrochemical detector had different sensitivities (slope of the calibration curve) to different organics in regards of μM concentration. The sensitivity decreased in the order of sucrose, GGA, glucose and glutamic acid. This is because the organic compounds contribute different number of electrons (n=4y−2j+m−3k−q) in the exhaustive oxidation reactions. With the decrease of transferred electrons per mole, i.e. sucrose (n=48), GGA (n=42), glucose (n=24) and glutamic acid (n=18), the organic compounds give fewer electrons per mole and hence the sensitivity decreases. This explained the sensitivity order in FIG. 14a. With the transferred electron number (n), the concentrations of the organic compounds were converted from μM to theoretical COD value in ppm. The same sensitivities, evidenced with the same slope, were obtained for the selected organics in FIG. 14b. This implied that the photoelectrochemical detector oxidised the above organics to the same extent, i.e. the organic compounds have been oxidised indiscriminately and the mineralisation was achieved. The detection principle was therefore validated. These is shown by plotting the PECOD values against the theoretical COD values as shown in FIG. 14c using glucose trendline as standard calibration curve. The line of best fit has a slope of 1.0268 and $R^2$ of 0.9984, which directly demonstrated that suitability to use glucose as a calibration standard to determine COD value for the unknown sample.

It was found that the detection limit of 0.5 ppm COD with a linear range up to 60 ppm COD can be achieved under the experimental conditions employed using glucose as testing analyte. The detection limit can be extended further by increasing the sample injection volume while the linear range can be increased by a further smaller injection volume.

Reproducibility and stability are important parameters for the usefulness of the detector. The response reproducibility of the sensor to 100 μM glucose was studied using repeated determinations (n=12) and RSD % was found to be 0.8%.

The detector is relatively stable. Significant baseline shift was observed for the first two hours when the electrode was brand new due to some of the active $TiO_2$ particles were not attached on the electrode surface enough firmly and was removed by the carrier. The baseline became almost constant after these non-stable active sites were removed. In fact all the data reported in this paper was obtained from the same $TiO_2$ electrode. The electrode had experience the change of pH (from 2 to 10), the change of potential (−0.4 to +0.8V), the change of flow rate, the change of injection volume and analysis of real samples and finished nearly thousand of the measurements it is still relatively sensitive and stable. When the electrode was not being used, it is filled with Milli-Q water and store in the light. It is well known that $TiO_2$ surface has merits of self-cleaning and super hydrophilicity. The fouling of electrode, which is commonly caused by adsorption of organic compounds and growth of bacteria, was not observed after storage. Because of this, even after a few days, it needed only about 5 minutes to regenerate the used electrode to acquire a stable baseline to start the detection of COD again.

Example 7

PECOD vs COD

The pH of the real samples tested in this example was in the range of 5-9, which is the pH independent region of the photoelectrochemical detector. Standard calibration curve method was used to determine the COD value in real sample. FIG. 15 shows the typical response of the flow injection response using glucose as the standard substance. As shown in the figure, both the charge (peak area, FIG. 15 (*a*)) and the peak current (peak height, FIG. 15 (*b*)) increased proportionally with the increase of glucose concentration. The calibration curve (the inserts of FIG. 15) was therefore constructed using the data from the above detection.

At the same time, the standard COD value was determined with conventional COD method (dichromate method). FIG. 16 shows the correlation between the experimental COD values and standard COD values. Where valid, the Pearson Correlation coefficient was used as a measure of the intensity of association between the values obtained from the flow injection photoelectrochemical COD method and the conventional COD method. This was employed for the data in FIG. 16. A highly significant correlation (r=0.991, P=0.000, n=13) between the two methods was obtained indicating the two methods agreed very well. More importantly, the slope of the principle axis of the correlation ellipse of 1.0819 was obtained. This almost unity slope value suggests both methods were accurately measuring the same COD value. Given a 95% confidence interval, this slope was between 1.016 and 1.174. This implies that we can be 95% confident that the true slope lies between these two values. Consider that there are analytical errors associated with both the flow injection photoelectrochemical COD and the standard method measurements and that these errors contribute to scatter on both axes, the strong correlation and slope obtained provides compelling support for the suitability of the flow injection photoelectrochemical COD method for measuring Chemical oxygen demand. The excellent agreements between the two COD values demonstrates the suitability for the proposed method to measure COD.

In FIGS. 17 to 21 various embodiments of the cell design are illustrated.

CONCLUSION

The present invention provides a COD analysis method, which is accurate, sensitive, environmentally friendly, robust, rapid and easy to be automated. This method in principle measures the theoretical COD value due to the extraordinary high oxidation power of photogenerated holes. The method described here is a direct method and independent of sample matrix. Under exhaustive degradation conditions, the method is an absolute method requires no calibration. Experimentally, it correlates well with the conventional dichromate method (Standard method). The electrode has a very good long time-stability, without showing any decline of photocatalytic activity. The nature of the analytical principle employed makes the method insensitive to the change of temperature. The method shows a good tolerance to temperature change in contrast to Karube's method. During the experiment the temperature did not controlled with the sample temperature ranging from 10 to 40° C., no photocurrent and charge change was observed.

Cell and Light Source Design

The method of this invention is capable of being carried out in a remote automatic analyser. As shown in FIG. 17 the equipment consists of an optical unit 2 a photochemical cell 3 which is connected to and controlled by the electrochemical unit 4. The supply system 5 provides electrolyte and samples at a prearranged dilution to the photochemical cell 2. The supply system includes reagent storage and waste disposal reservoirs as well as sample filtering and pre-treatment and dilution units. This system is controlled by the processing system hardware 7 which includes a processor 10 communicating through an analogue to digital and digital to analogue interface 8 with the electrochemical unit 4 as well as the supply system 5, the optical unit and the photo electrochemical cell 3. The hardware will also include a communication device to allow remote transmission of data to a central database. Additional analysis functions such as pH and temperature may be carried out by sensors 6 which are linked to the A/D D/A interface 8.

A first embodiment of the cell component is shown in 18. In all of FIGS. 18 to 221 the same reference numerals are used for the same components. In FIG. 18 the disposable component 20 consists of an electrode holder 22 and the titanium dioxide working photo electrode 21 which is disposable and is insertable into the insertion chamber 25 in the non disposable cell part 30 where it is held in place by the screws 37. The non disposable cell part includes sample inlet 31 and outlet 32 and in between them are the LED UV light source 40 and its quartz window 36, the reference electrode 33 with its associated porous frit 35, and the auxiliary electrode 34.

In FIG. 19 an alternative arrangement is shown where the disposable part 20 is attached to the base of the non disposable part 30 with a spacer gasket 23 set between them. The reaction chamber 26 as in all the embodiments is located between the working electrode 21 and the quartz window 36.

In the embodiment of FIG. 20 the whole of the cell is disposable except for the UV LED light source which is insertable into the docking space 41.

In FIG. 21*a* variation of the designs of FIGS. 18 and 19 is shown where the disposable part 20 fits into an insertion chamber 25 of the non disposable part 30. The working electrode 21 has an electrical connection 29 as shown in FIG. 21.

To provide for more efficient use of the LED UV light source a range of alternative designs are shown in FIGS. 22 to 25.

A Micro-Directivity Regulator (MDR) shown in FIG. 22 is a set of small size optical lenses that configures in a way that allows the maximum collection of output light from the LED source and regulates the collected light into a uniformly distributed-parallel light. When a MDR is combined with the LED light source, a large distance between the LED and the surface to be illuminated is allowed since the output light intensity becomes distance independent. The input light can be regulated into two different shapes of light beams. One is circular shape parallel beam and another is narrow-rectangular shape parallel beam.

Incorporation of an Optical Fibre Directivity Regulator (OFDR) as illustrated in FIG. 23 provides freedoms for changing both distance and direction. It also allows the end of the light source to be immersed in the solution, which provides addition flexibility for the design of a photoreactor.

The OFDR shown in FIG. 23 consists of two sets of optical lenses. One set is located at the reception end and another set is located at the output end of the OFDR. Simply by adding a cylindrical lens to the output end can change the shape of the output beam from circular shape into narrow-narrow-rectangular shape.

Many applications require simultaneously operating multiple photoreactors and for these an Optical Fibre Directivity Regulative Array (OFDRA) as shown in FIG. 24 may be used. Under some circumstances, large input light power is needed to increase the rate of reaction or reduce the time required for the completion of the reaction. As shown in FIG. 25 an OFDRA is capable of applying combined output powers of the OFDRA to a single reactor in a form of long-narrow continuous rectangular shape beam.

Whilst the description of the invention utilises a three electrode photochemical cell it will be appreciated that the photoelectrochemical cell may comprise a working electrode ($TiO_2$) and a counter electrode, wherein the counter electrode may suitably act as both a counter electrode and a reference electrode.

Throughout the specification the aim has been to describe the preferred embodiments of the invention without limiting the invention to any one embodiment or specific collection of features.

Throughout this specification, unless the context requires otherwise, the word "comprises", and variations such as "comprise" or "comprising", will be understood to imply the inclusion of a stated integer or group of integers or steps but not to the exclusion of any other integer or group of integers.

The invention claimed is:

1. A method of determining chemical oxygen demand of a water sample under non exhaustive degradation conditions, comprising the steps of
   a) applying a constant potential bias to a thin layer photoelectrochemical cell, having a photoactive nanoparticulate semiconductive working electrode and a counter electrode, and containing a supporting electrolyte solution;
   b) illuminating the working electrode with a light source and recording the background photocurrent produced at the working electrode from the supporting electrolyte solution;
   c) adding a 5 μl to 200 μl of water sample, to be analysed, to the photoelectrochemical cell;
   d) illuminating the working electrode with a light source and recording the total photocurrent produced with the sample;
   e) deducting the back ground photocurrent from the total photocurrent produced with the sample to obtain the net photocurrent due to the oxidation of organic material in the sample
   f) determining the chemical oxygen demand of the water sample according to the following sequence of computations $i_{Isample} = nFAk[COD]_{sample} = K[COD]_{sample}$ $i_{Istandard} = nFAk\{[COD]_{sample} + [COD]_{standard}\} = K\{[COD]_{sample} + [COD]{standard}\}$ Where
   K=nFAk is a constant for given experimental conditions
   n=number of electrons transferred during the photoelectrochemical degradation,
   F=Faraday constant,
   A=active electrode area,
   k=mass-transfer coefficient; and $$[COD]_{sample} = \frac{i_{Isample}}{i_{Istandard} - i_{Isample}} \times [COD]_{standard}.$$

2. A method as claimed in claim 1 in which the working electrode is a layer of titanium dioxide nanoparticles coated on an inert conductive substrate.

3. A method as claimed in claim 1 in which a reference electrode is also used in addition to the working and counter electrodes.

4. A method as claimed in claim 1 in which the sample is diluted with the supporting electrolyte solution.

5. A method as claimed in claim 1 in which the chemical oxygen demand is determined with a stationary or flow cell using different operational modes including batch mode, flow-stopped mode and continuous flow mode.

6. A thin layer photoelectrochemical assay apparatus for determining oxygen demand of a water sample under non exhaustive degradation conditions which consists of
   a) a measuring cell for holding 5 μl to 200 μl of a sample to be analysed
   b) a photoactive nanoparticulate semiconductive working electrode and a counter electrode disposed in said cell,
   c) a light source adapted to illuminate the photoactive working electrode
   d) control means to control the illumination of the working electrode, the applied potential bias, and photocurrent recording
   e) photocurrent measuring means to measure the photocurrent at the working electrode
   f) analysis means to derive a measure of oxygen demand according to the following sequence of computations $i_{Isample} = nFAk[COD]_{sample} = K[COD]_{sample}$ $i_{Istandard} = nFAk\{[COD]_{sample} + [COD]_{standard}\} = K\{[COD] + [COD]\}$ Where
   K=nFAk is a constant for given experimental conditions
   n=number of electrons transferred during the photoelectrochemical degradation,
   F=Faraday constant, A=active electrode area,
k=mass-transfer coefficient; and $$[COD]_{sample} = \frac{i_{Isample}}{i_{Istandard} - i_{Isample}} \times [COD]_{standard}.$$

7. Apparatus as claimed in claim 6 in which a reference electrode is included in the measuring cell.

8. Apparatus as claimed in claim 6 in which the working electrode is a layer of titanium dioxide nanoparticles on an inert substrate.

9. Apparatus as claimed in claim 6 which also includes a reservoir for a supporting electrolyte which is used to measure the background photocurrent and to dilute the sample.

10. Apparatus as claimed in claim 9 which also includes a sample supply/injection system and a supporting electrolyte supply/injection system.

11. Apparatus as claimed in claim 6 in which the working electrode is adapted to be insertable and removable.

12. Apparatus as claimed in claim 6 in which the light source is an ultraviolet light emitting diode.

13. Apparatus as claimed in claim 12 in which the light is passed through a direction regulator to ensure even light distribution over the photo catalyst surface.

14. Apparatus as claimed in claim 13 in which optical fibres are used to convey the light to the photo catalyst surface.

15. An electrochemical reaction thin layer cell for use in the apparatus of claim 6 which consists of
   a) cell body containing a sample inlet and a sample outlet
   b) a socket for an ultraviolet light emitting diode unit
   c) a reference electrode
   d) an optionally removable working electrode of titanium dioxide nanoparticles on an inert substrate.
   e) a reaction chamber located between the working electrode and the socket for an ultraviolet light emitting diode unit.

16. Apparatus as claimed in claim 6 which also includes a reservoir for a supporting electrolyte which is used to measure the background photocurrent and to dilute the sample.

17. Apparatus as claimed in claim 8 which also includes a reservoir for a supporting electrolyte which is used to measure the background photocurrent and to dilute the sample.

* * * * *